(12) United States Patent
Barletta

(10) Patent No.: US 12,364,500 B2
(45) Date of Patent: Jul. 22, 2025

(54) TISSUE RESECTING INSTRUMENT

(71) Applicant: Covidien LP, Mansfield, MA (US)

(72) Inventor: Steven J. Barletta, Tewksbury, MA (US)

(73) Assignee: COVIDIEN LP, Mansfield, MA (US)

( * ) Notice: Subject to any disclaimer, the term of this patent is extended or adjusted under 35 U.S.C. 154(b) by 551 days.

(21) Appl. No.: 17/751,770

(22) Filed: May 24, 2022

(65) Prior Publication Data

US 2022/0378458 A1 Dec. 1, 2022

Related U.S. Application Data

(60) Provisional application No. 63/193,322, filed on May 26, 2021.

(51) Int. Cl.
*A61B 17/32* (2006.01)
*A61B 90/98* (2016.01)

(52) U.S. Cl.
CPC ........ *A61B 17/32002* (2013.01); *A61B 90/98* (2016.02); *A61B 2017/320032* (2013.01); *A61B 2017/32004* (2013.01)

(58) Field of Classification Search
CPC .............. A61B 17/32; A61B 17/32002; A61B 17/320783; A61B 17/320016; A61B 2017/320028; A61B 2017/320032; A61B 2017/320024; A61B 2017/32004; A61B 2017/347; A61B 2017/0023; A61B 2017/00398; A61B 2017/00424;

(Continued)

(56) References Cited

U.S. PATENT DOCUMENTS

| 1,585,934 A | 5/1926 | Muir |
| 1,666,332 A | 4/1928 | Hirsch |

(Continued)

FOREIGN PATENT DOCUMENTS

| DE | 3339322 A1 | 5/1984 |
| DE | 3206381 C2 | 7/1986 |

(Continued)

OTHER PUBLICATIONS

Extended European Search Report issued in corresponding European Application No. 21169301.5 dated Sep. 22, 2021, 8 pages.

*Primary Examiner* — Liesl C Baumann
*Assistant Examiner* — Alexis D Amechi
(74) *Attorney, Agent, or Firm* — Carter, DeLuca & Farrell LLP

(57) ABSTRACT

An end effector assembly of a tissue-resecting device is disclosed. The end effector assembly includes an outer shaft and an inner shaft. The outer shaft includes an outer shaft window defined within a distal end portion thereof. The outer shaft window defines an outer shaft cutting edge extending about at least a portion of a perimeter thereof. The outer shaft cutting edge includes a plurality of teeth. The inner shaft is disposed within and rotatable relative to the outer shaft, and includes an inner shaft window defined within a distal end portion thereof. The inner shaft window defines a toothless inner shaft cutting edge extending about at least a portion of a perimeter thereof. Rotation of the inner shaft relative to the outer shaft causes the inner shaft cutting edge to rotate toward the outer shaft cutting edge.

20 Claims, 15 Drawing Sheets

(58) Field of Classification Search
CPC .. A61B 2017/0046; A61B 2017/00477; A61B 2017/00734; A61B 2017/4216; A61B 2017/00482; A61B 17/42; A61B 2090/034; A61B 2090/035; A61B 90/90; A61B 90/98; A61B 90/92; A61B 90/94; A61B 90/96; A61B 2217/005; A61B 2217/007; A61B 34/37
See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |

(56) References Cited

U.S. PATENT DOCUMENTS

| | | |
|---|---|---|
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,251,120 B1 | 6/2001 | Dorn |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,157,826 B2 | 4/2012 | Deng et al. |
| 8,419,626 B2 | 4/2013 | Shener-Irmakoglu et al. |
| 8,444,592 B2 | 5/2013 | Williams et al. |
| 8,465,421 B2 | 6/2013 | Finkman et al. |
| 8,500,769 B2 | 8/2013 | Deng |
| 8,528,563 B2 | 9/2013 | Gruber |
| 8,568,424 B2 | 10/2013 | Shugrue et al. |
| 8,574,253 B2 | 11/2013 | Gruber et al. |
| 8,597,228 B2 | 12/2013 | Pyles et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,474,848 B2 | 10/2016 | Williams et al. |
| 10,376,278 B2 | 8/2019 | Fojtik et al. |
| 2003/0093103 A1* | 5/2003 | Malackowski ........ A61B 34/20 606/170 |
| 2006/0196038 A1* | 9/2006 | Van Wyk ......... A61B 17/32002 29/557 |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2012/0191119 A1* | 7/2012 | Hedstrom ........ A61B 17/32002 606/171 |
| 2013/0131452 A1 | 5/2013 | Kuroda et al. |
| 2014/0003183 A1 | 1/2014 | Song |
| 2015/0305765 A1 | 10/2015 | Fojtik et al. |
| 2016/0066945 A1* | 3/2016 | Nguyen ........... A61B 17/32002 606/180 |
| 2017/0189046 A1 | 7/2017 | Fojtik et al. |
| 2019/0038305 A1* | 2/2019 | Smith ................. A61B 90/39 |
| 2020/0129225 A1* | 4/2020 | Marshall .......... A61B 17/32002 |

FOREIGN PATENT DOCUMENTS

| | | |
|---|---|---|
| DE | 3601453 A1 | 9/1986 |
| DE | 3615694 A1 | 11/1987 |

(56) References Cited

FOREIGN PATENT DOCUMENTS

| | | |
|---|---|---|
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| EP | 3868316 A1 | 8/2021 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

\* cited by examiner

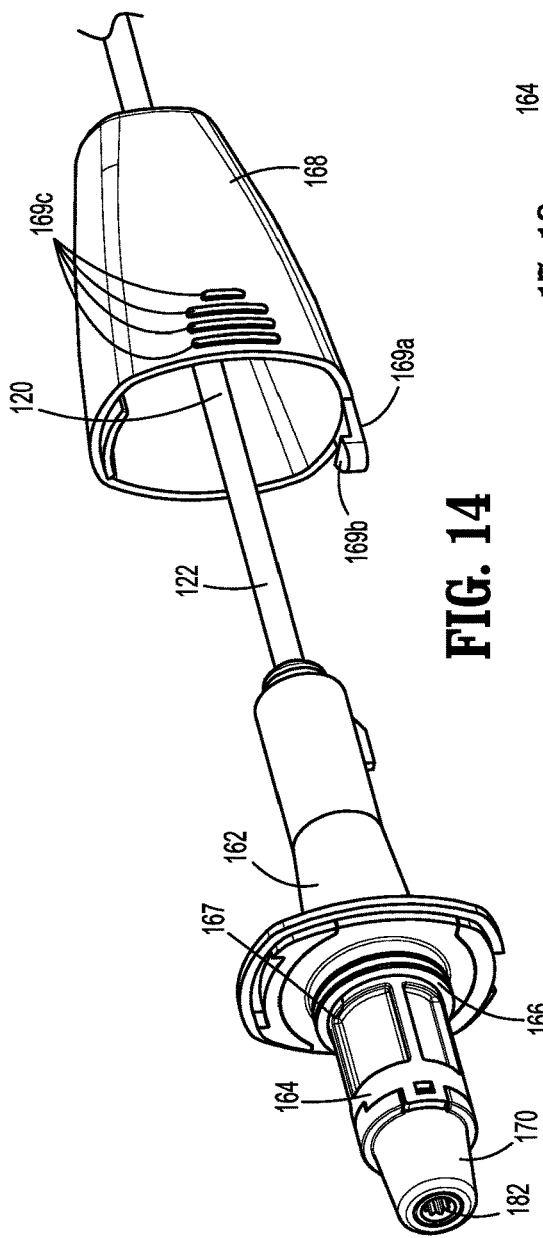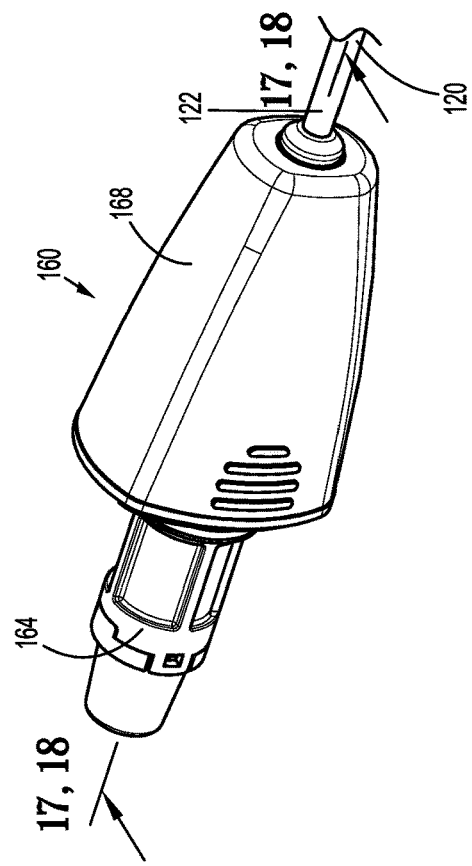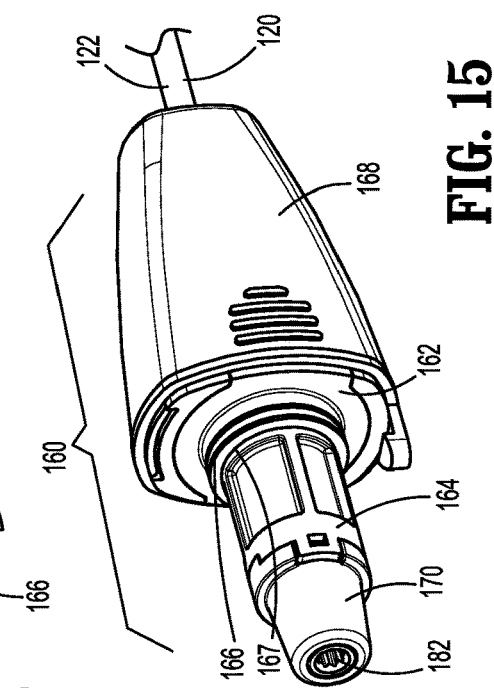

TISSUE RESECTING INSTRUMENT

CROSS REFERENCE TO RELATED APPLICATION

This application claims the benefit of and priority to U.S. Provisional Patent Application Ser. No. 63/193,322, filed on May 26, 2021, the entire contents of which are incorporated by reference herein.

BACKGROUND

Technical Field

The present disclosure relates generally to the field of tissue resection. In particular, the present disclosure relates to a tissue resecting instrument configured to facilitate resection and removal of tissue from an internal surgical site, e.g., a uterus.

Background of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

The present disclosure relates to an end effector assembly of a tissue-resecting device. The end effector assembly includes an outer shaft and an inner shaft. The outer shaft includes a proximal end portion, a distal end portion, and an outer shaft window defined within the distal end portion. The outer shaft window defines an outer shaft cutting edge extending about at least a portion of a perimeter thereof. The outer shaft cutting edge includes a plurality of teeth. The inner shaft is disposed within and rotatable relative to the outer shaft, and includes a proximal end portion, a distal end portion, and an inner shaft window defined within the distal end portion. The inner shaft window defines a toothless inner shaft cutting edge extending about at least a portion of a perimeter thereof. Rotation of the inner shaft relative to the outer shaft causes the inner shaft cutting edge shaft to rotate toward the outer shaft cutting edge.

In an aspect of the present disclosure, a distal end of the outer shaft window is disposed proximally of a distal-most end of the outer shaft. In aspects, the distal-most end of the outer shaft is blunt.

In another aspect of the present disclosure, the distal end portion of the inner shaft includes only one inner shaft cutting edge.

In another aspect of the present disclosure, the distal end portion of the outer shaft includes an outer shaft slot disposed opposite the outer shaft window.

In still another aspect of the present disclosure, the distal end portion of the inner shaft includes an inner shaft slot disposed opposite the inner shaft window at a proximal end of the distal end portion of the inner shaft.

In yet another aspect of the present disclosure, the inner shaft cutting edge defines a length, and an entirety of the length of the inner shaft cutting edge is defined by a single curve.

In still yet another aspect of the present disclosure, the inner shaft includes a distal driver disposed about a proximal end portion thereof. In aspects, the end effector assembly also includes a proximal driver slidably coupled to the distal driver in a fixed rotational orientation relative thereto such that rotation of the proximal driver drives rotation of the distal driver. In aspects, the end effector assembly includes a retainer cap defining a pocket having an open end. The retainer cap is disposed about at least a portion of the proximal driver and is fixedly engaged with a hub housing of the outer shaft to thereby fix the retainer cap relative to the hub housing and the outer shaft. The retainer cap is configured to selectively lock the proximal driver in fixed rotational orientation relative thereto, thereby selectively locking the inner shaft relative to the outer shaft.

In another aspect of the present disclosure, the end effector assembly includes a radiofrequency identification (RFID) chip disposed within the pocket, such that when the retainer cap is engaged with the hub housing, a portion of the hub housing closes the open end of the pocket to retain the RFID chip therein.

In still another aspect of the present disclosure, the end effector assembly includes a biasing spring extending between the proximal driver and the distal driver. The biasing spring is configured to bias the proximal driver towards a locked position. The retainer cap locks the proximal driver in fixed rotational orientation relative thereto. In aspects, the proximal driver is movable against the bias of the biasing spring to an unlocked position, and the proximal driver is unlocked from the retainer cap to permit relative rotation therebetween.

The present disclosure also relates to a tissue resecting instrument including a handpiece assembly and an end effector assembly. The end effector assembly extends distally from the handpiece assembly, defines a longitudinal axis, and includes an elongated outer shaft and an elongated inner shaft. The elongated outer shaft has a distal end portion with an outer shaft window defined therein. The outer shaft window includes a plurality of teeth surrounding at least a portion of a perimeter thereof. The elongated inner shaft is disposed coaxially with the outer shaft, and has a distal end portion with an inner shaft window defined therein. The inner shaft window is at least partially bounded by a toothless inner shaft cutting edge. The inner shaft is rotatable about the longitudinal axis relative to the outer shaft such that the inner shaft cutting edge rotates toward the plurality of teeth of the outer shaft.

In an aspect of the present disclosure, the handpiece assembly includes an outflow port configured to connect to a fluid management system.

In another aspect of the present disclosure, the handpiece assembly includes a motor configured to cause rotation of the inner shaft relative to the outer shaft.

In another aspect of the present disclosure, a distal end of the window of the outer shaft is disposed proximally of a distal-most end of the outer shaft.

In still another aspect of the present disclosure, the distal end portion of the inner shaft includes only one inner shaft cutting edge.

In yet another aspect of the present disclosure, the distal end portion of the outer shaft includes an outer shaft slot disposed opposite the outer shaft window.

In still yet another aspect of the present disclosure, the inner shaft cutting edge defines a length, and an entirety of the length of the inner shaft cutting edge is defined by a single curve.

BRIEF DESCRIPTION OF THE DRAWINGS

Various aspects of the present disclosure are illustrated herein with reference to the accompanying drawings, wherein:

FIG. 14 is a rear, perspective view illustrating proximal insertion of an outer shell about the portion of the end effector assembly illustrated in FIG. 13;

FIG. 15 is a rear, perspective view of a proximal end portion of the end effector assembly of FIG. 1 in an assembled condition;

FIG. 16 is a side, perspective view of the proximal end portion of the end effector assembly of FIG. 1 in the assembled condition;

DETAILED DESCRIPTION

As used herein, the term "distal" refers to the portion of the instrument that is described which is farther from a user, while the term "proximal" refers to the portion that is described which is closer to a user. Further, to the extent consistent, any or all of the aspects described herein may be used in conjunction with any or all of the other aspects described herein.

Figure 1:
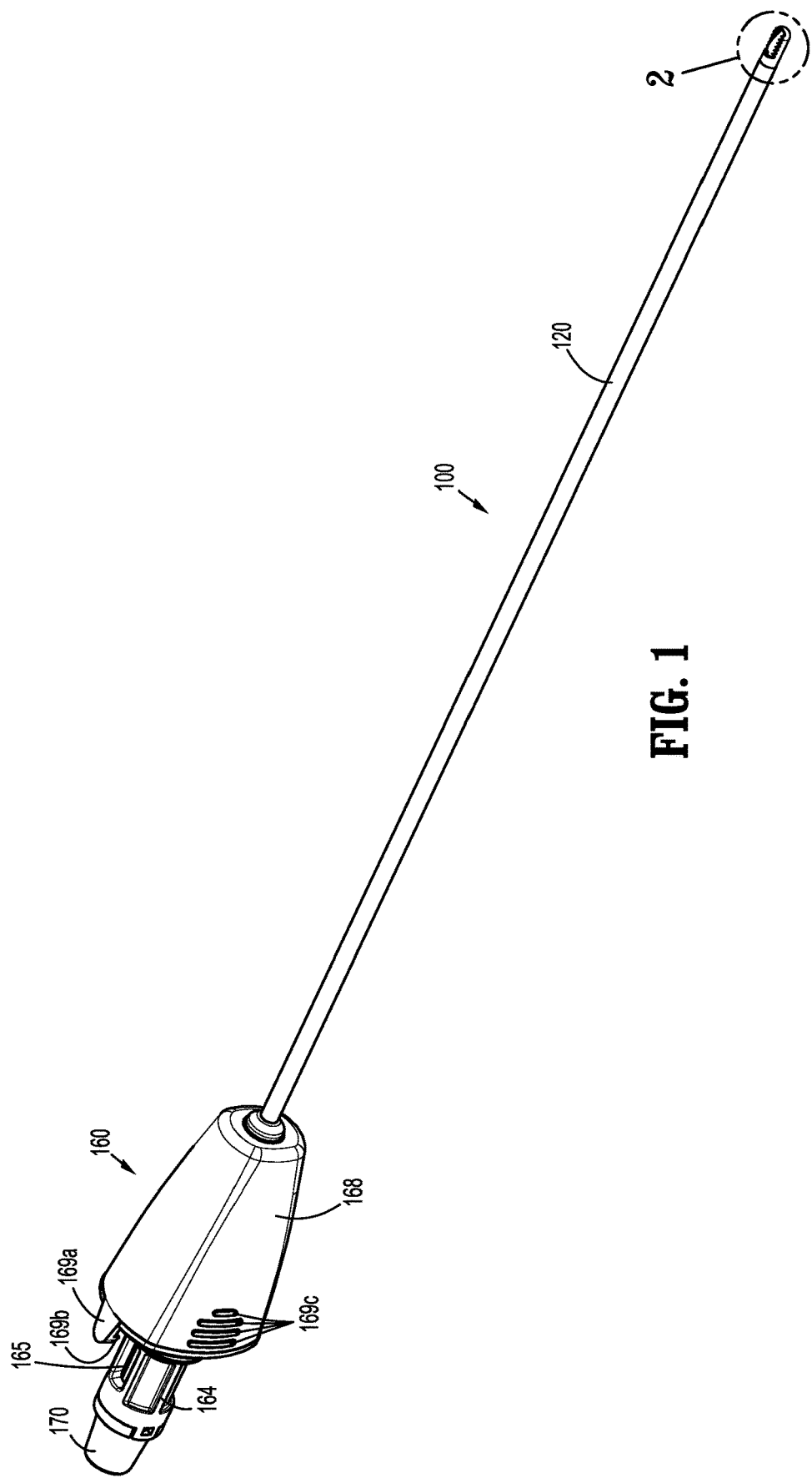
FIG. 1 is a side, perspective view of an end effector assembly of a tissue resecting instrument provided in accordance with aspects of the present disclosure wherein an inner shaft of the end effector assembly is disposed in a first position.
Figure 19:
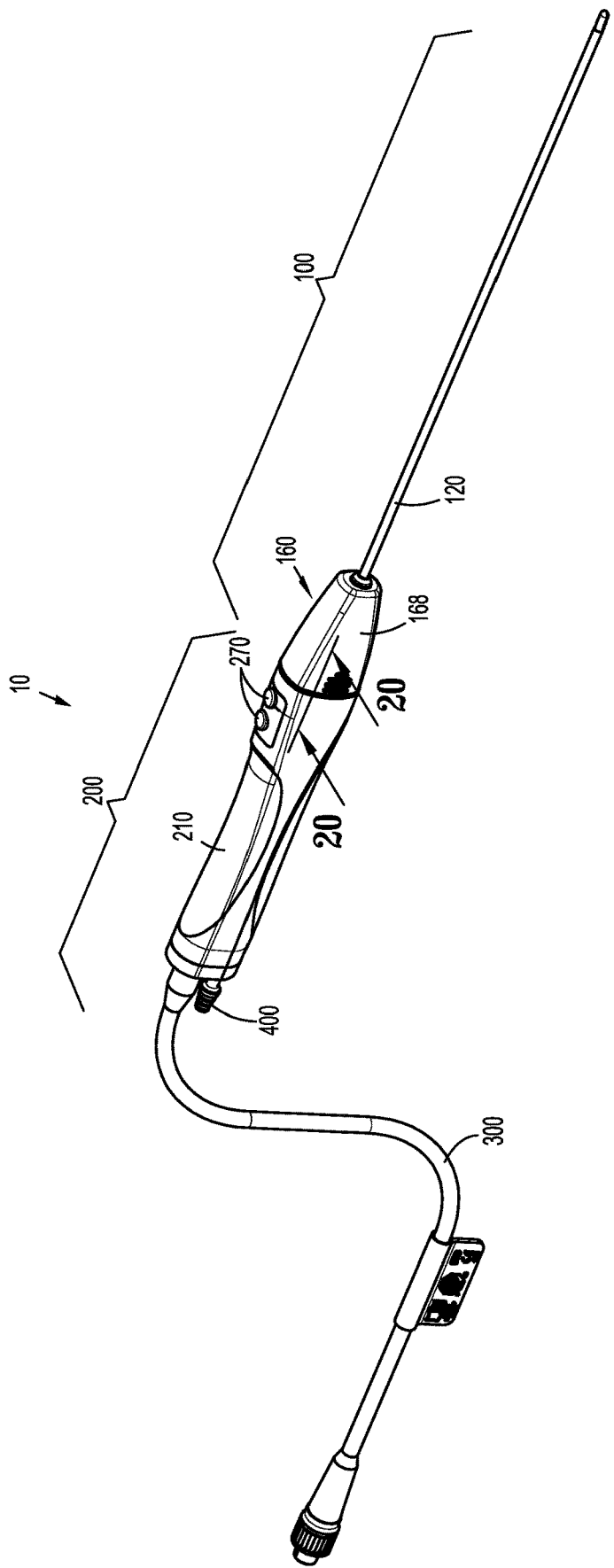
FIG. 19 is a side, perspective view of a tissue resecting instrument including the end effector assembly of FIG. 1 engaged with a handpiece.

Referring generally to FIGS. 1 and 19, a tissue resecting instrument 10 provided in accordance with the present disclosure and configured to resect tissue includes an end effector assembly 100 and a handpiece assembly 200. The tissue resecting instrument 10 is adapted to connect to a control unit (not shown) via a cable 300 to provide power and control functionality to tissue resecting instrument 10, although tissue resecting instrument 10 may alternatively or additionally include a power source, e.g., battery, and/or a control unit within or configured to mechanically engage the handpiece assembly 200. Tissue resecting instrument 10 is further adapted to connect to a fluid management system (not shown) via outflow tubing (not shown) connected to an outflow port 400 for applying suction to remove fluid, tissue, and debris from a surgical site via tissue resecting instrument 10. The control unit and fluid management system may be integral with one another, coupled to one another, or separate from one another.

Tissue resecting instrument 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use and partially-reusable configurations, handpiece assembly 200 may be configured as a cleanable/sterilizable, reusable component, while end effector assembly 100 is configured as a single-use, disposable/reprocessable component. In any of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for interchangable use of different end effector assemblies, e.g., different length, configuration, etc., end effector assemblies, with handpiece assembly 200.

Figure 2:
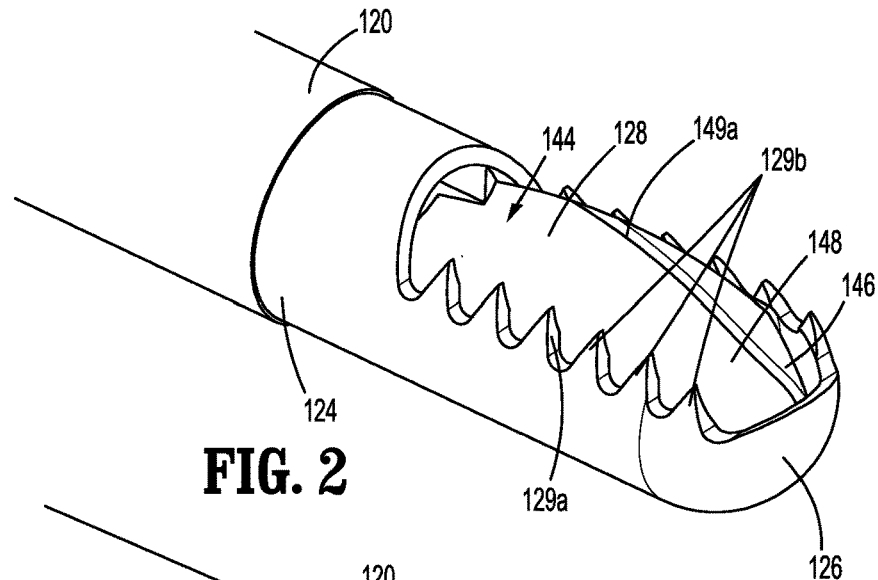
FIG. 2 is an enlarged, perspective view of the area of detail indicated as "2" in FIG. 1.
Figure 3:
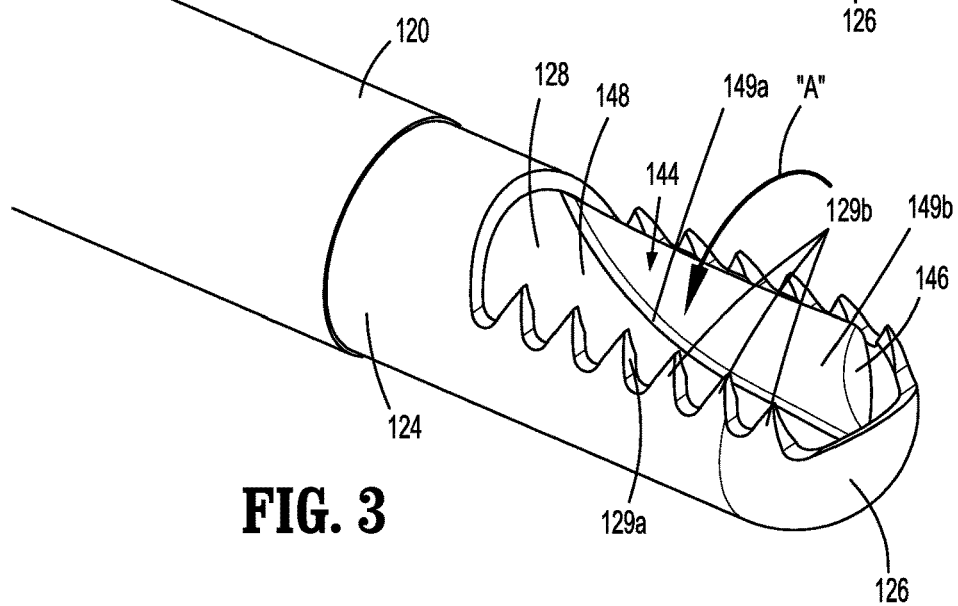
FIG. 3 is an enlarged, perspective view of a distal end portion of the end effector assembly of FIG. 1, wherein the inner shaft of the end effector assembly is disposed in a second position.
Figure 4:
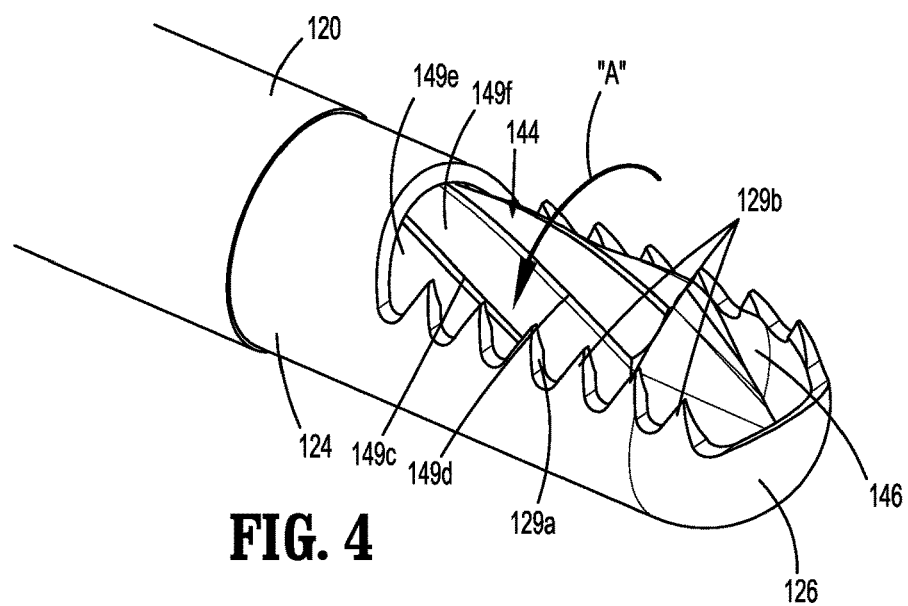
FIG. 4 is an enlarged, perspective view of the distal end portion of the end effector assembly as illustrated in FIG. 3, wherein the inner shaft of the end effector assembly is disposed in a third position.

With reference to FIGS. 2-5, end effector assembly 100 includes an outer shaft 120, an inner shaft 140, a hub assembly 160, a drive assembly 180, and an RFID chip 190. The outer shaft 120 includes a proximal end portion 122 and a distal end portion 124. With particular reference to FIGS. 2-4, the distal end portion 124 defines an at least partially closed distal end 126 and a transverse outer shaft window 128 disposed adjacent the at least partially closed distal end 126. The outer shaft window 128 provides access to the interior of outer shaft 120 transversely through a sidewall thereof. Additionally, in the embodiment shown in FIGS. 2-4, for instance, outer shaft window 128 is at least partially surrounded by an outer shaft cutting edge 129a about the outer perimeter of outer shaft window 128 so as to facilitate cutting of tissue passing through outer shaft window 128 and into outer shaft 120. The outer shaft cutting edge 129a may define a serrated configuration including a plurality of cutting teeth 129b extending along longitudinal sides of outer shaft window 128 or may define any other suitable configuration. In embodiments, cutting teeth 129b are arcuate in configuration to conform to the tubular shape of outer shaft 120.

Figure 8:
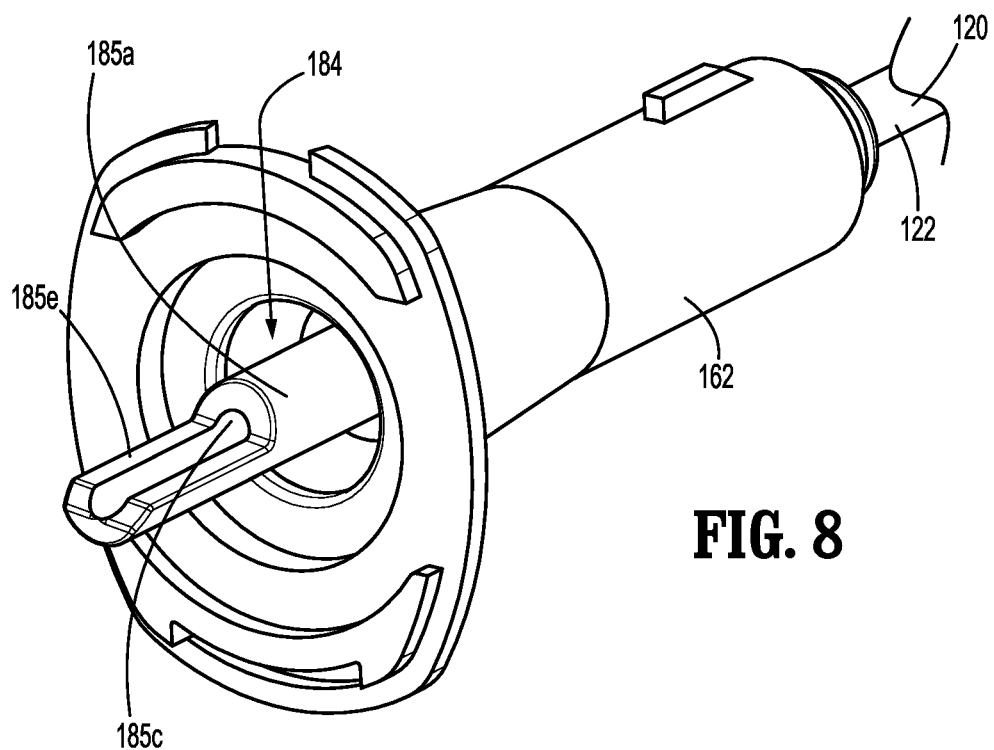
FIG. 8 is a rear, perspective view of the portion of the end effector assembly illustrated in FIG. 6 assembled within the portion of the end effector assembly illustrated in FIG. 7.

Inner shaft 140 is rotatably disposed within outer shaft 120 and includes a proximal end portion 142 (FIG. 5) and a distal end portion 144 defining an at least partially closed distal end 146 and a transverse inner shaft window 148 disposed adjacent the at least partially closed distal end 146. The inner shaft window 148 provides access to a lumen 185c defined by inner shaft 140 (FIGS. 6 and 8). The distal end portion 144 may further include an inner shaft cutting edge 149a positioned adjacent inner shaft window 148 to facilitate cutting tissue passing through inner shaft window 148 and into lumen 185c defined by inner shaft 140. The inner shaft cutting edge 149a defines a curved configuration (relative to a longitudinal axis defined through end effector assembly 100), and may further define a cutting flute or channel 149b configured for rotational cutting removal of tissue. Additionally, in the embodiment illustrated in FIGS. 2-4, an entirety of the length of the inner shaft cutting edge 149a is defined by a single curve and lacks teeth.

With particular reference to FIG. 4, the distal end portion 144 of the inner shaft 140 may also include additional surfaces 149c, 149d along the body of the inner shaft 140. The surfaces 149c, 149d are the intersection between adjacent facets, which may result from the process of machining the inner shaft 140. Also, faces 149e, 149f are formed between inner shaft cutting edge 149a and surface 149c, and between surfaces 149c and 149d. The faces 149e, 149f may be helpful to direct cut tissue out through the inner shaft window 148, for instance. More or fewer faces and channels may be included without departing from the scope of the disclosure. For instance, it is envisioned that the distal end portion 144 of the inner shaft 140 includes a single face.

Referring now to FIG. 6, the distal end portion 144 of the inner shaft 140 may also include an inner shaft slot 145 disposed proximally of the inner shaft cutting edge 149a. The inner shaft slot 145 may be useful to provide increased flow of fluid and transfer of tissue to the lumen 185c defined by inner shaft 140, for instance.

With reference to FIGS. 1-4, inner shaft 140 is configured for rotation within and relative to outer shaft 120 to thereby rotate inner shaft window 148 relative to outer shaft window 128. More specifically, inner shaft 140 is configured to rotate in the general direction of arrow "A" between a first position (FIG. 2), a second position (FIG. 3), and a third position (FIG. 4). In the first position, as illustrated in FIG. 2, outer shaft window 128 and inner shaft window 148 are at least partially radially aligned with one another to enable drawing of tissue through outer shaft window 128 and inner shaft window 148, under suction, thereby facilitating the cutting of tissue extending into inner shaft 140 as inner shaft 140 is rotated relative to outer shaft 120. The applied suction also facilitates removal of tissue, fluids, and debris through inner shaft 140, as detailed below.

In the second position, as illustrated in FIG. 3, inner shaft 140 is rotated relative to outer shaft 120 from the first position illustrated in FIG. 2 such that outer shaft window 128 and inner shaft window 148 are no longer radially aligned with one another but still define a passageway therethrough into inner shaft 140. In the third position, as illustrated in FIG. 4, inner shaft 140 is rotated further relative to outer shaft 120 from the second position illustrated in FIG. 3 such that outer shaft window 128 and inner shaft window 148 are fully misaligned, e.g., do not overlap, from one another to close the passageway into inner shaft 140. Moving to the third position, e.g., a closed position, and fully misaligning outer shaft window 128 and inner shaft window 148 helps ensure that tissue that had been pulled through outer shaft window 128 and inner shaft window 148 is fully separated to enable removal from the surgical site through tissue resecting instrument 10.

Figure 21:
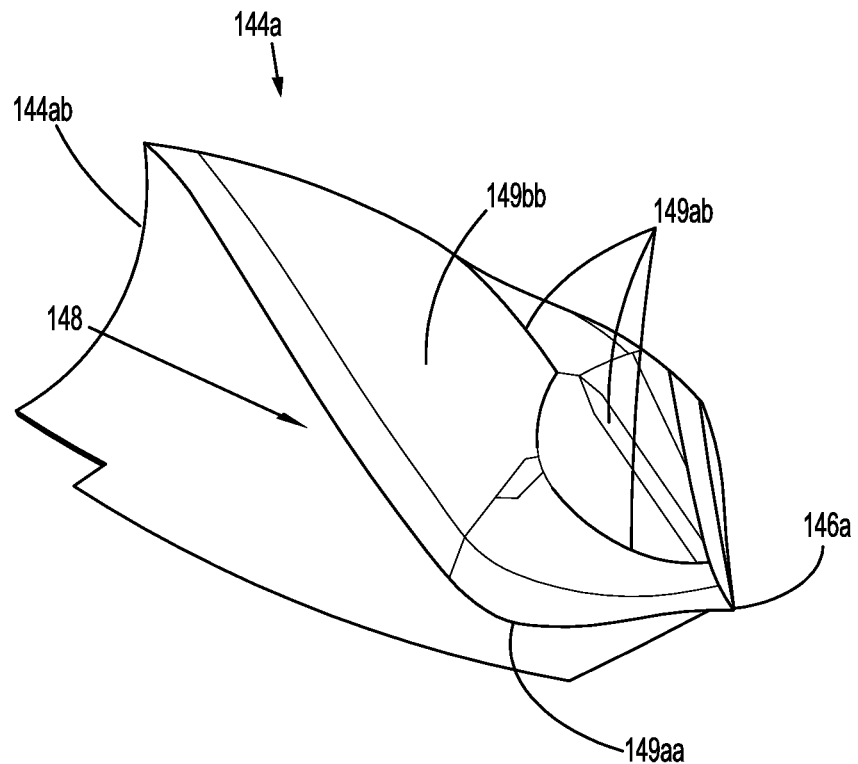
FIGS. 21 and 22 are perspective views of a second embodiment of a distal end portion of the inner shaft of the end effector assembly.
Figure 22:
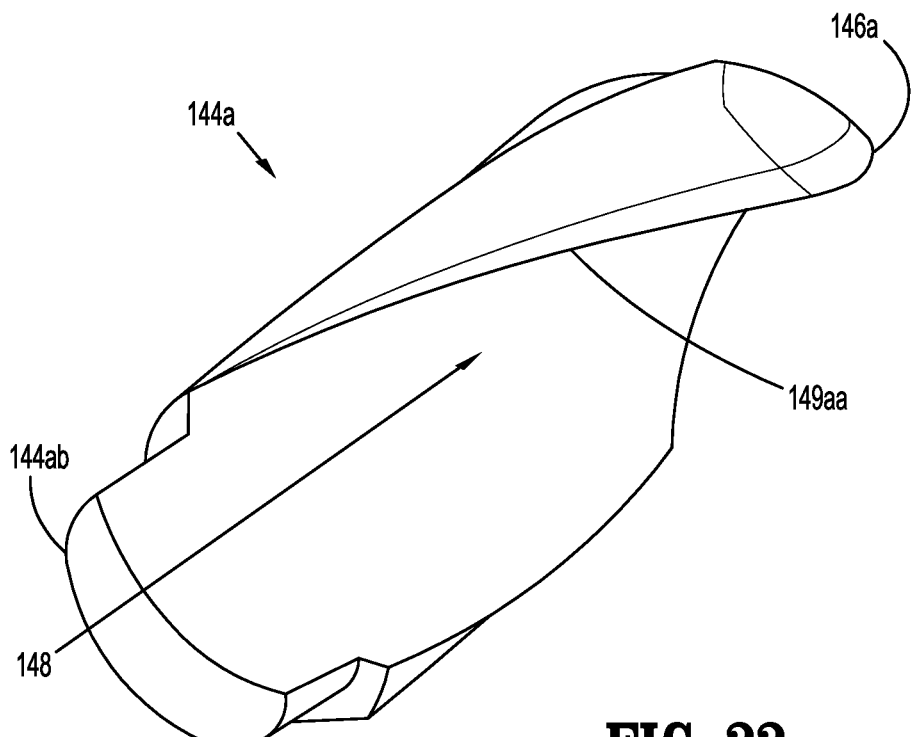

FIGS. 21-27 illustrate various embodiments of distal end portion 124 of outer shaft 120, and distal end portion 144 of inner shaft 140. In particular, FIGS. 21 and 22 are perspective views of a second embodiment of a distal end portion 144a of inner shaft 140. In this embodiment, a distal-most end 146a of distal end portion 144a includes part of an inner shaft cutting edge 149aa and defines a pointed tip. Additionally, as most clearly shown in FIG. 21, inner shaft cutting edge 149aa is continuous from distal-most end 146a through a proximal end 144ab of distal end portion 144a. Similar to the embodiment of distal end portion 144 of FIGS. 2-4, distal end portion 144a may also include additional surfaces 149ab, and/or at least one face 149bb.

Figure 23:
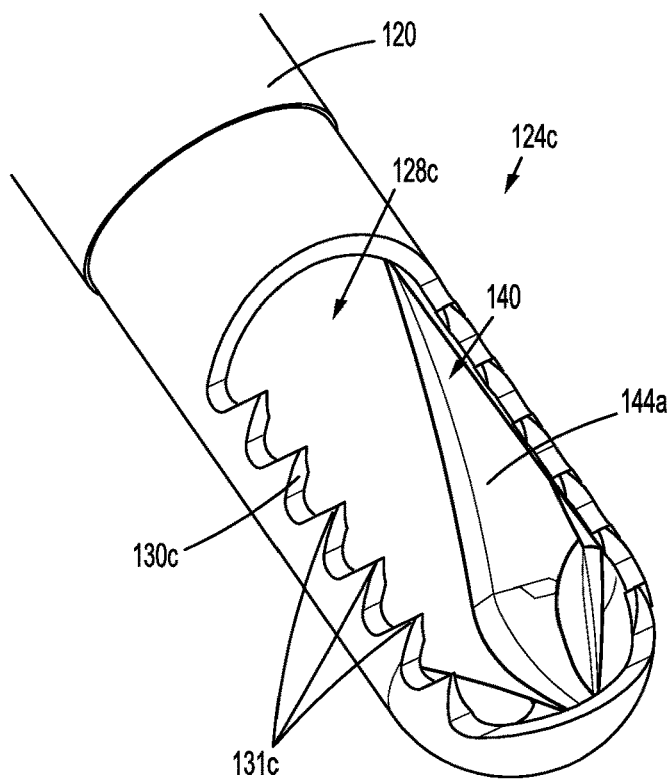
FIG. 23 is a perspective view of a distal portion of a second embodiment of the end effector assembly including teeth and a slot, and engaged with the inner shaft of FIGS. 21 and 22.
Figure 24:
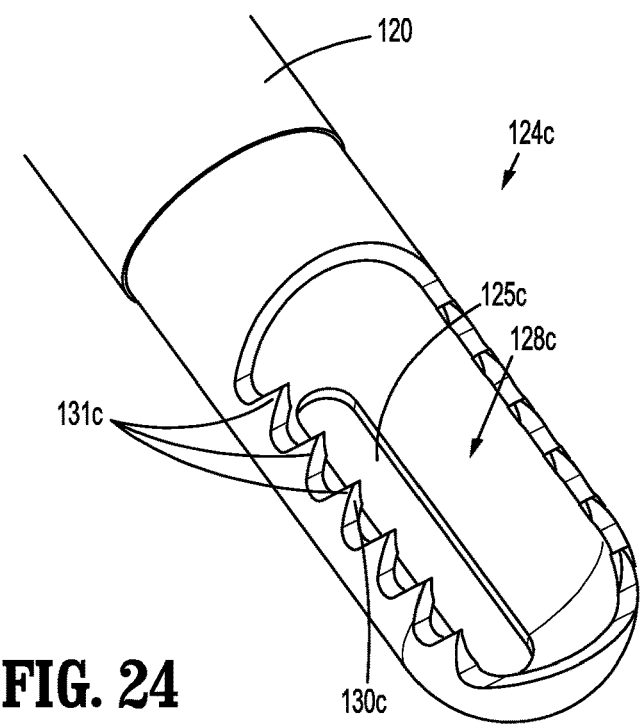
FIG. 24 is a perspective view of the distal portion of the second embodiment of the end effector assembly of FIG. 23 with the inner shaft omitted.

With reference to FIGS. 23 and 24, a second embodiment of distal end portion 124c of outer shaft 120 is shown. FIG. 23 illustrates distal end portion 124c of outer shaft 120 with distal end portion 144a of inner shaft 140 of FIGS. 21 and 22 therein. FIG. 24 shows distal end portion 124c of outer shaft 120 with the inner shaft 140 omitted. Distal end portion 124c of outer shaft 120 defines an outer shaft window 128c which provides access to the interior of outer shaft 120 transversely through a sidewall thereof and is surrounded by an outer shaft cutting edge 130c about the outer perimeter of outer shaft window 128c so as to facilitate cutting of tissue passing through outer shaft window 128c and into outer shaft 120. Outer shaft cutting edge 130c defines a serrated configuration including a plurality of cutting teeth 131c extending along longitudinal sides of outer shaft window 128c. As shown, cutting teeth 131c are arcuate in configuration to conform to the tubular shape of outer shaft 120. Additionally, distal end portion 124c of outer shaft 120 includes an outer shaft slot 125c disposed therein. The outer shaft slot 125c may be useful to provide increased flow of fluid and transfer of tissue to the interior of outer shaft 120, for instance.

Figure 25:
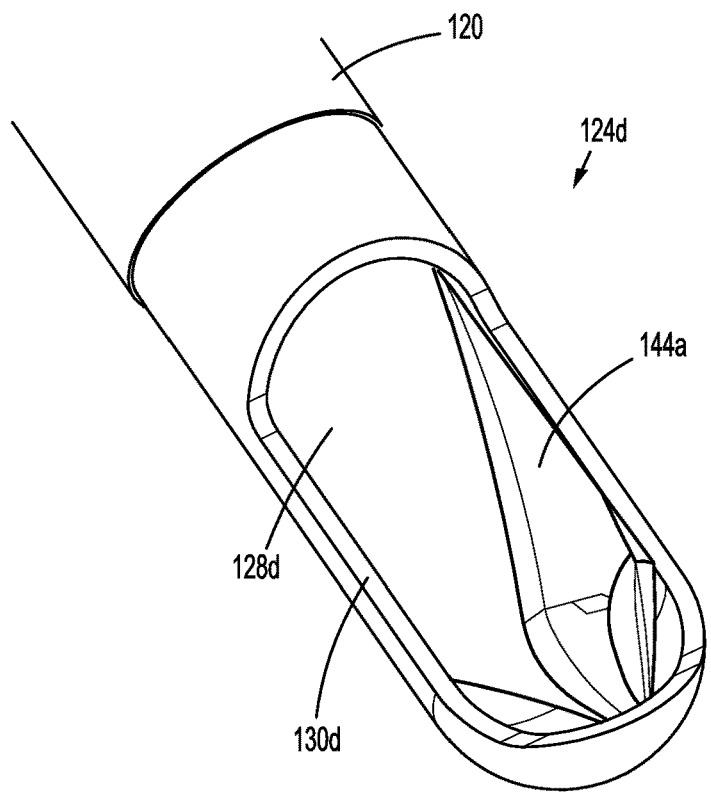
FIG. 25 is a perspective view of a distal portion of a third embodiment of a the end effector assembly which includes neither teeth nor a slot, and engaged with the inner shaft of FIGS. 21 and 22.
Figure 26:
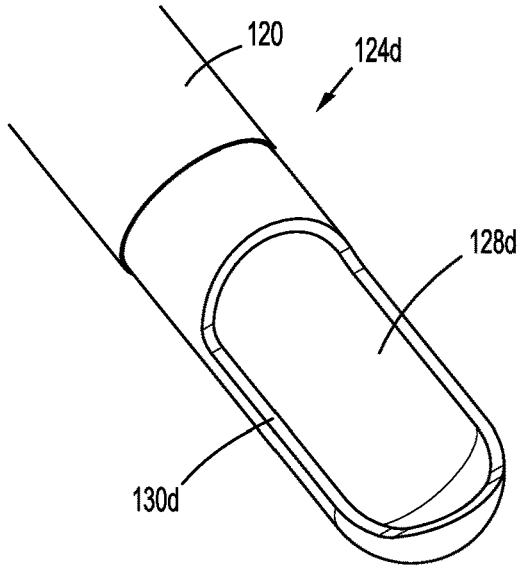
FIG. 26 is a perspective view of the distal portion of the third embodiment of the end effector assembly of FIG. 25 with the inner shaft omitted.

With reference to FIGS. 25 and 26, a third embodiment of distal end portion 124d of outer shaft 120 is shown. FIG. 25 illustrates distal end portion 124d of outer shaft 120 with distal end portion 144a of inner shaft 140 of FIGS. 21 and 22 therein. FIG. 26 shows distal end portion 124d of outer shaft 120 with the inner shaft 140 omitted. Distal end portion 124d of outer shaft 120 defines an outer shaft window 128d which provides access to the interior of outer shaft 120 transversely through a sidewall thereof and is surrounded by an outer shaft cutting edge 130d about the outer perimeter of outer shaft window 128d so as to facilitate cutting of tissue passing through outer shaft window 128d and into outer shaft 120. Outer shaft cutting edge 130d defines a continuous curve and lacks teeth.

Figure 27:
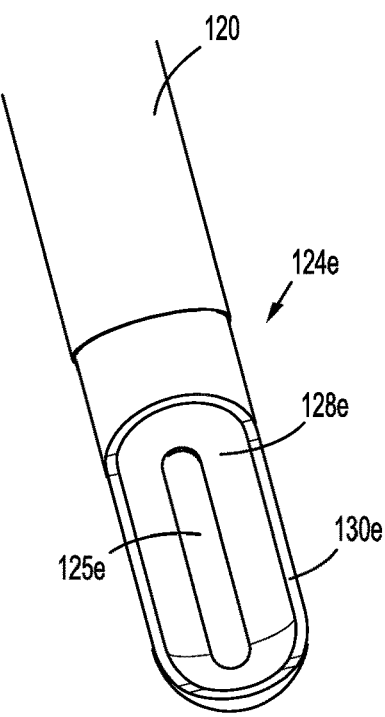
FIG. 27 is a perspective view of a distal portion of a fourth embodiment of the end effector assembly including a slot and no teeth, with the inner shaft omitted.

Referring to FIG. 27, a fourth embodiment of distal end portion 124e of outer shaft 120 is shown. Distal end portion 124e is similar to distal end portion 124d of FIGS. 25 and 26, as distal end portion 124e defines an outer shaft window 128e having an outer shaft cutting edge 130e. Additionally, distal end portion 124e includes an outer shaft slot 125e disposed therein. The outer shaft slot 125e may be useful to provide increased flow of fluid and transfer of tissue to the interior of outer shaft 120, for instance.

Other suitable configurations of various components of outer shaft 120 and/or inner shaft 140 that cooperate to facilitate tissue cutting are also contemplated. For instance, while a single direction (clockwise) of rotation of inner shaft 140 is shown, it is further contemplated that various components of end effector assembly 100, such as but not limited to inner shaft 140, can be modified such that inner shaft 140 can be rotated in a counter-clockwise direction to cut tissue.

Figure 5:
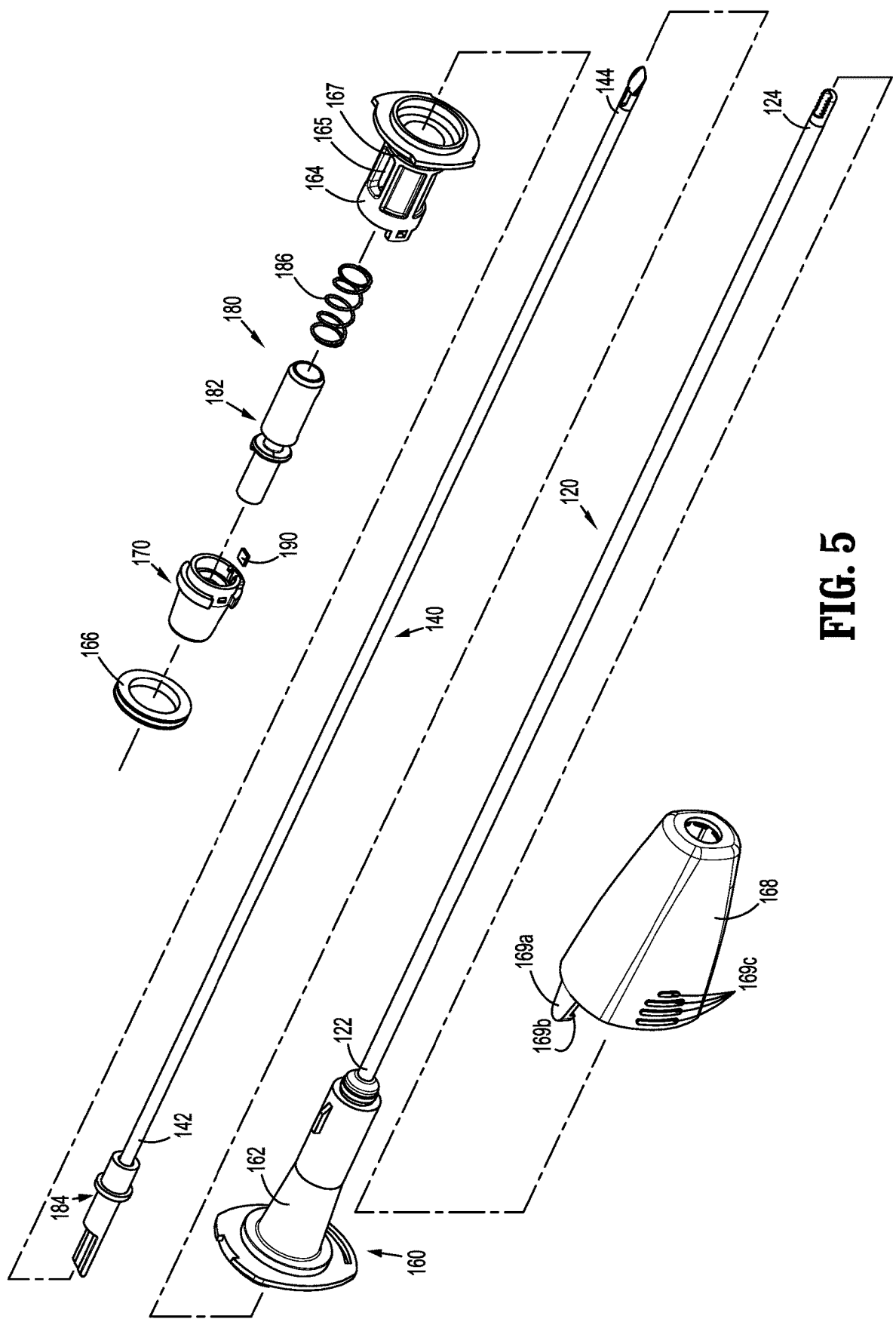
FIG. 5 is a side, perspective, exploded view of the end effector assembly of FIG. 1.
Figure 6:
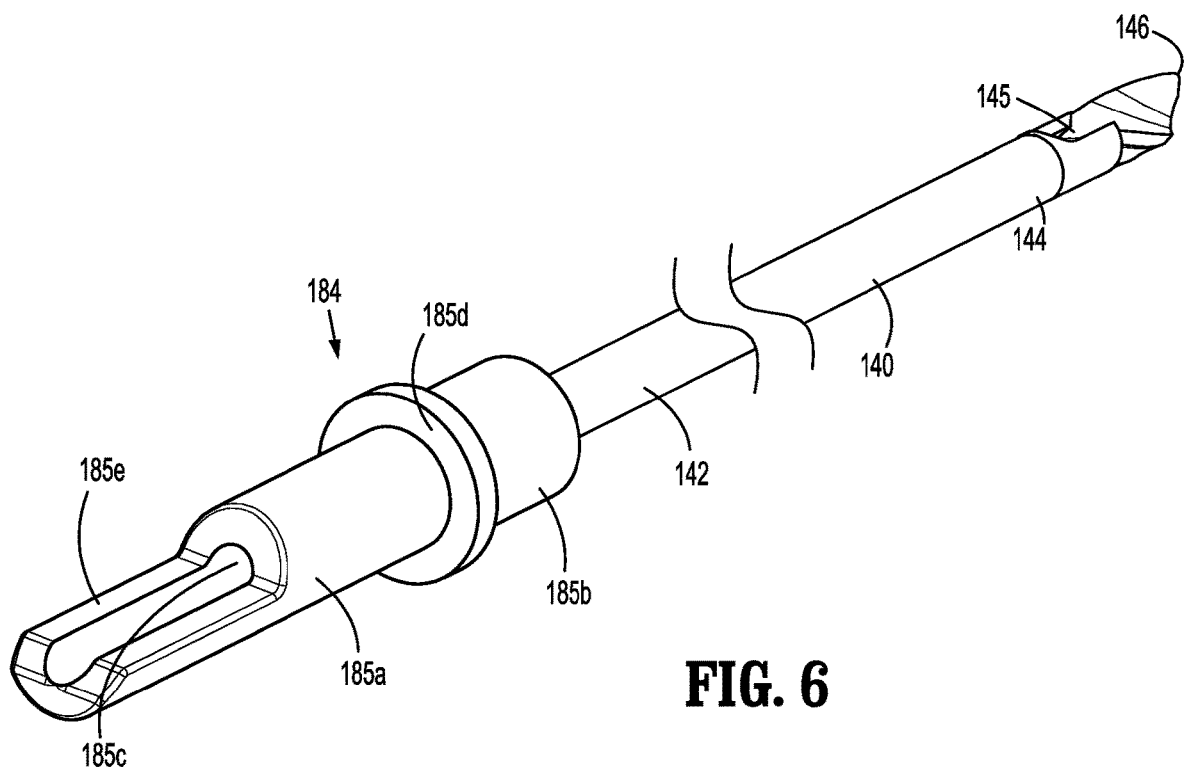
FIG. 6 is a rear perspective view of the inner shaft of the end effector assembly of FIG. 1 including a distal driver assembled thereon.

With reference to FIGS. 1 and 5, as noted above, end effector assembly 100 includes outer shaft 120, inner shaft 140, hub assembly 160, and drive assembly 180. End effector assembly 100 further includes RFID chip 190 captured between a retainer cap 170 of hub assembly 160 and a proximal extension portion 164 of a hub housing 161 of hub assembly 160, as detailed below.

Figure 20:
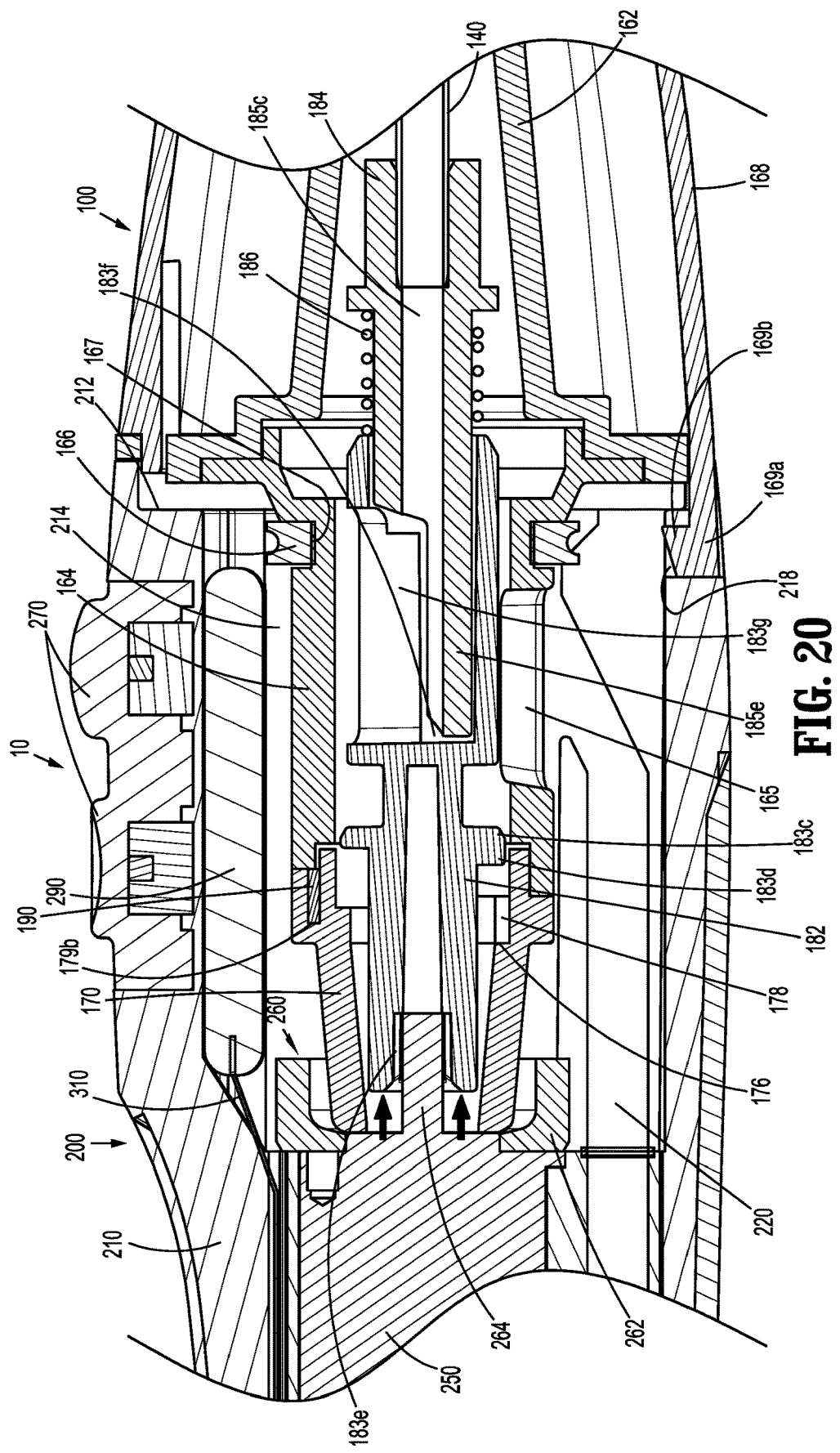
FIG. 20 is a longitudinal, cross-sectional view taken across section line "20-20" of FIG. 19.

Hub assembly 160 includes a hub housing 161 having a distal body portion 162 and a proximal extension portion 164 that are configured for engagement with one another, e.g., via snap-fitting or other suitable engagement. Referring momentarily to FIGS. 19 and 20, with end effector assembly 100 engaged with handpiece assembly 200, proximal extension portion 164 of hub housing 161 extends into handpiece assembly 200 while distal body portion 162 substantially abuts and extends distally from handpiece assembly 200. Proximal extension portion 164 of hub housing 161 further defines an outflow opening 165 through a sidewall thereof that is configured to fluidly communicate with an internal bore 214 of handle housing 210 of handpiece assembly 200 when end effector assembly 100 is engaged therewith.

Figure 7:
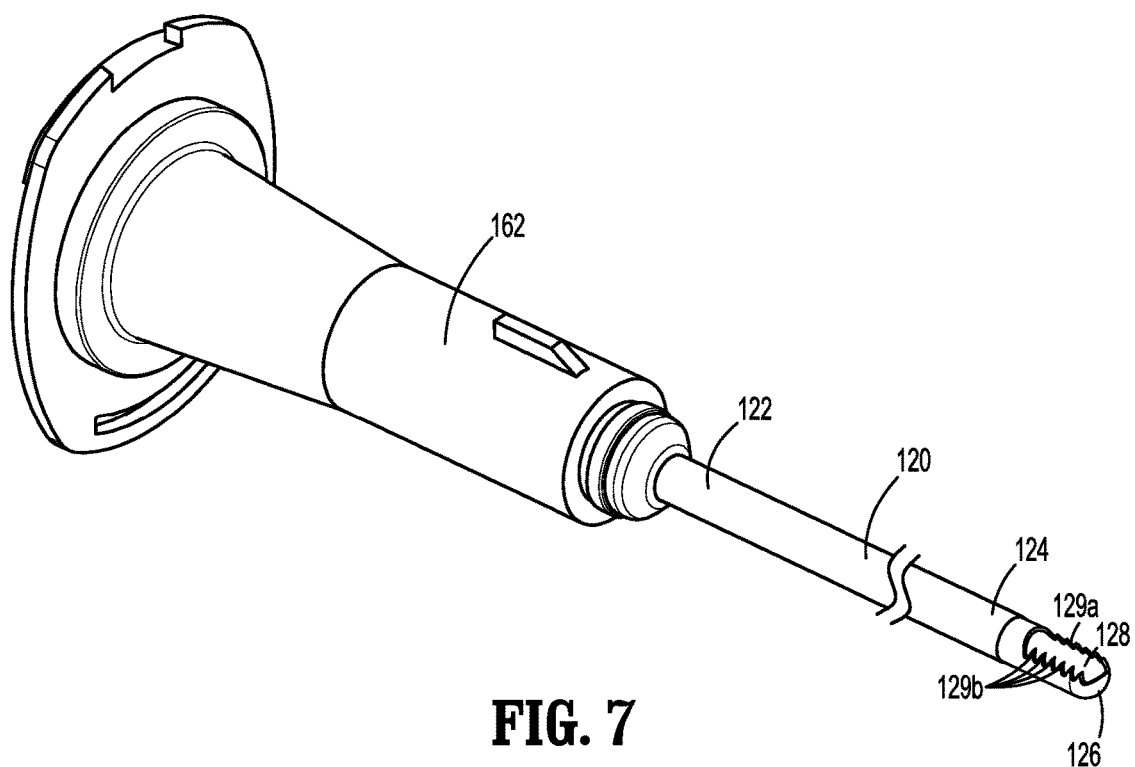
FIG. 7 is a side, perspective view of an outer shaft of the end effector assembly of FIG. 1 including a distal body portion of a hub housing assembled thereon.

Returning to FIGS. 1 and 5, and with additional reference to FIGS. 7 and 8, distal body portion 162 of hub housing 161 is fixedly disposed about proximal end portion 122 of outer shaft 120 with outer shaft 120 extending distally therefrom. Inner shaft 140 extends through outer shaft 120, as noted above, and extends proximally through distal body portion 162 of hub housing 161 into proximal extension portion 164 of hub housing 161 wherein drive assembly 180 is operably coupled to proximal end portion 142 of inner shaft 140.

Figure 12:
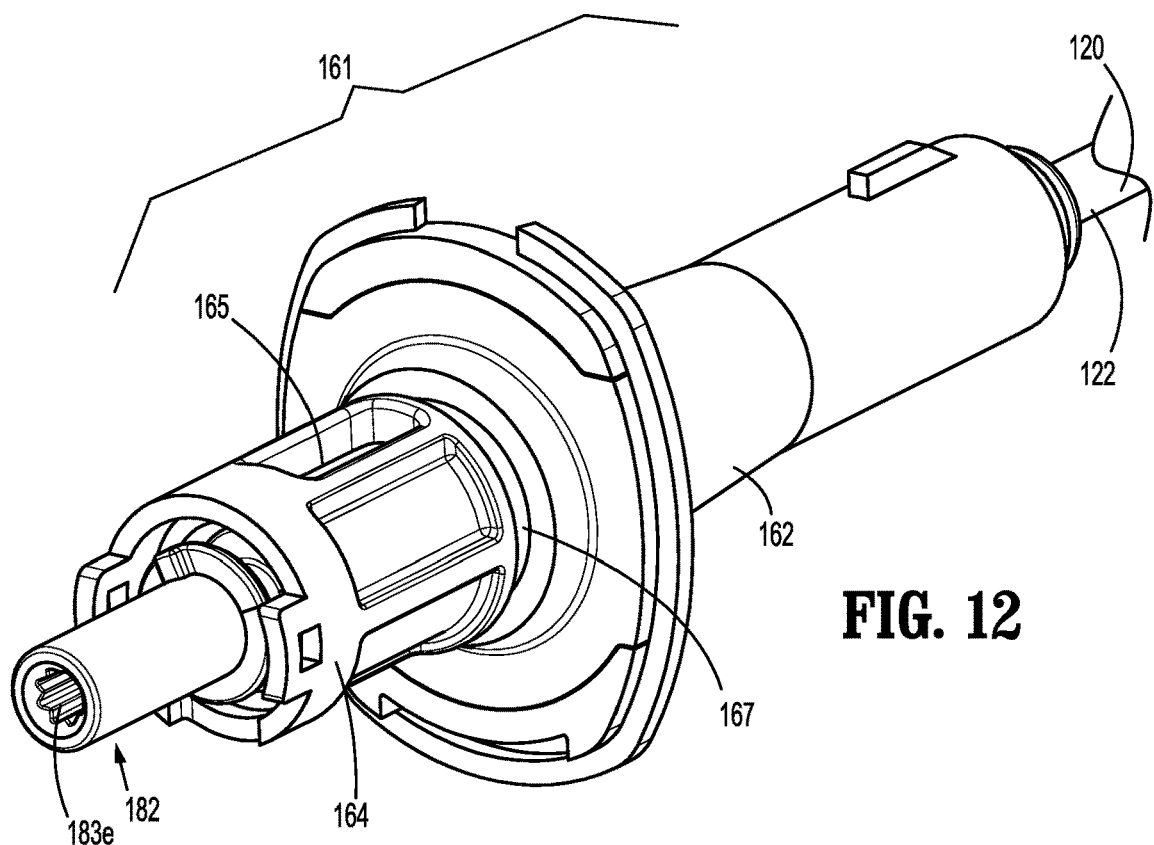
FIG. 12 is a rear, perspective view of the portion of the end effector assembly illustrated in FIG. 9, further including a proximal extension portion of the hub housing assembled thereto.
Figure 17:
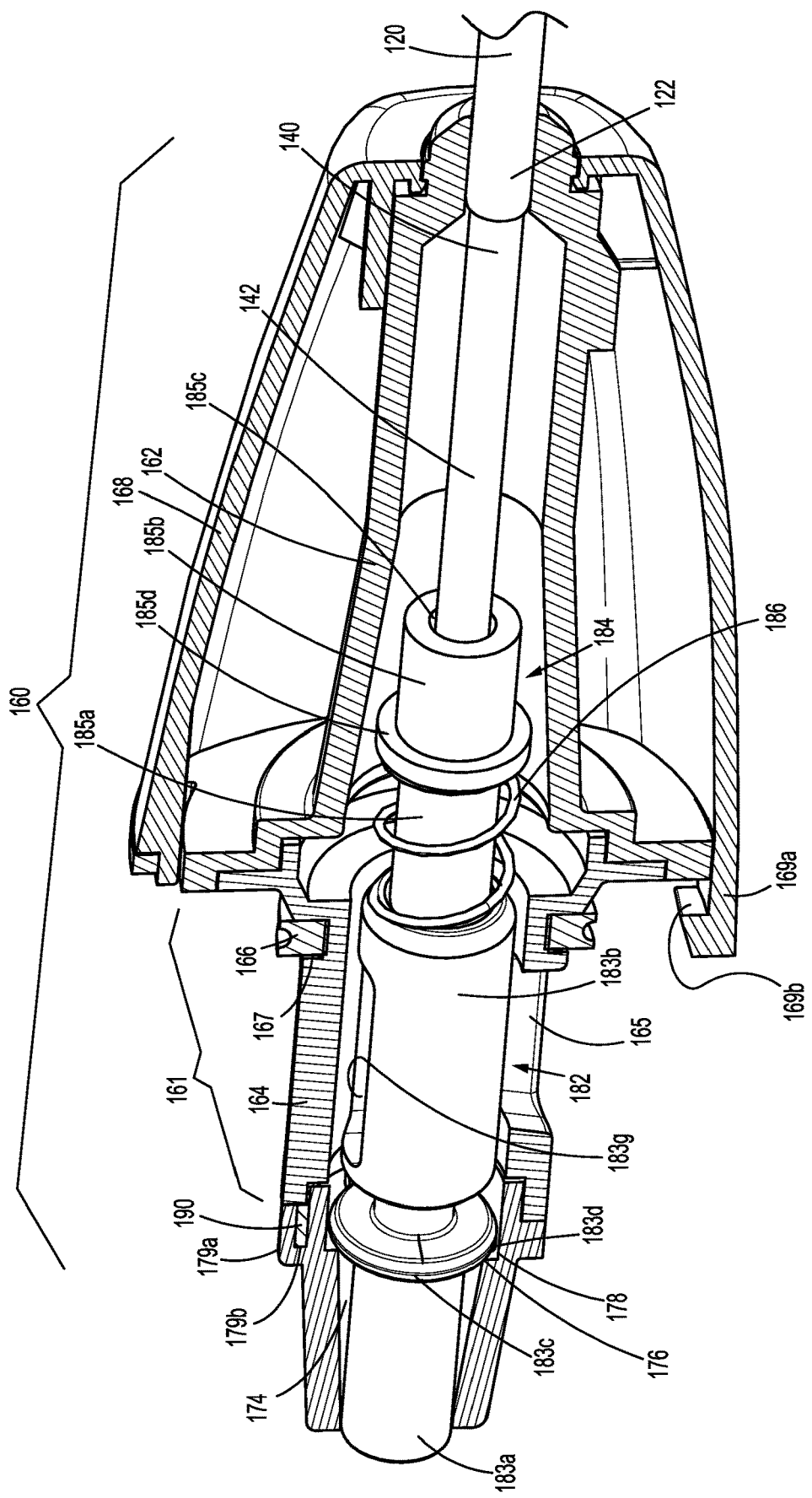
FIG. 17 is a perspective, longitudinal, partial cross-sectional view taken across section line "17-17" of FIG. 16.
Figure 18:
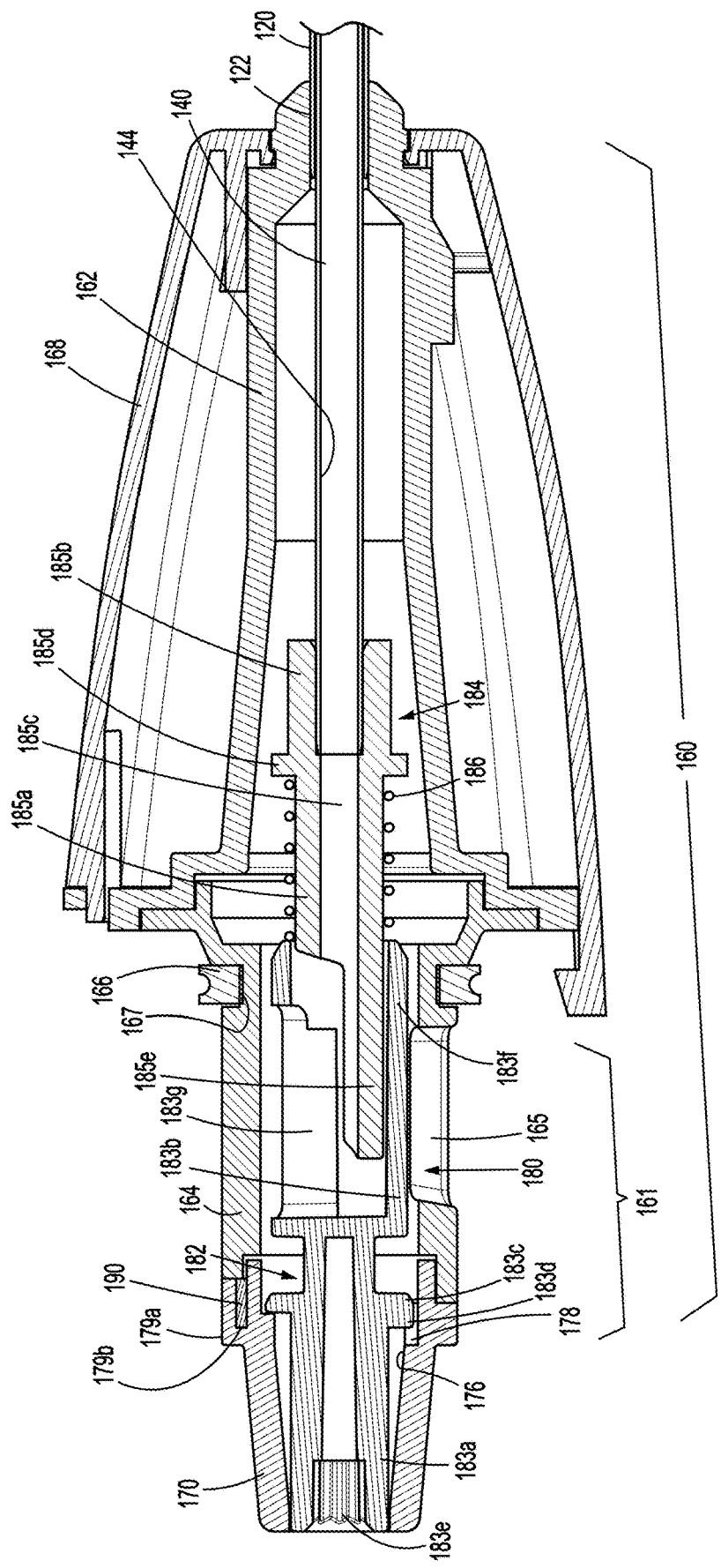
FIG. 18 is a longitudinal, cross-sectional view taken across section line "18-18" of FIG. 16.

Referring also to FIGS. 12, 17, and 18, hub assembly 160 further includes an O-ring 166 configured for engagement about proximal extension portion 164 of hub housing 161 distally of outflow opening 165. O-ring 166, as illustrated in FIG. 20, is configured to establish a fluid-tight seal against the interior of handle housing 210 of handpiece assembly 200 when end effector assembly 100 is engaged therewith to inhibit fluid from travelling distally after exiting outflow opening 165.

With reference to FIGS. 5 and 14-18, hub assembly 160 additionally includes an outer shell 168 configured for positioning about distal body portion 162 of hub housing 161 and for engagement therewith, e.g., via snap-fit engagement or in any other suitable manner. A cantilever engagement finger 169a extends proximally from a lower surface of outer shell 168 of hub housing 161 and proximally from distal body portion 162 of hub housing 161 when outer shell 168 is engaged thereabout. Engagement finger 169a includes an engagement tooth 169b extending therefrom that is configured for engagement within a corresponding aperture 218 defined within handle housing 210 of handpiece assembly 200 (see FIG. 20) to enable releasable engagement of end effector assembly 100 with handpiece assembly 200 (FIG. 20). Grasping ribs 169c are defined on side surfaces of outer shell 168 to facilitate engagement and disengagement of end effector assembly 100 to and from handpiece assembly 200 (FIG. 20).

With reference to FIGS. 5 and 10-13, retainer cap 170 of hub assembly 160 is configured for snap-fit or other suitable engagement with a proximal end portion of proximal extension portion 164. Retainer cap 170 defines a longitudinal lumen 174 extending through retainer cap 170. An internal collar 176 protrudes radially inwardly into longitudinal lumen 174. Internal collar 176 includes a distally-oriented notch 178 defined therein. Retainer cap 170 further includes an external collar 179a defining a pocket 179b. Pocket 179b is configured to receive RFID chip 190 therein. When retainer cap 170 is engaged with proximal extension portion 164, e.g., via snap-fitting, the open end of pocket 179b is blocked by a proximal face of proximal extension portion 164, thereby capturing RFID chip 190 therein.

Referring to FIGS. 5, 6, 9, 11, 12, 17 and 18, drive assembly 180 is configured to operably couple drive rotor 260 of handpiece assembly 200 (see FIG. 20) with inner shaft 140 such that rotation of drive rotor 260 (FIG. 20) drives rotation of inner shaft 140 within and relative to outer shaft 120. Drive assembly 180, more specifically, includes a proximal driver 182, a distal driver 184, and a biasing spring 186, e.g., a coil compression spring. In some embodiments, drive assembly 180 further includes a threaded coupler and cam follower (not shown) operable to convert rotation of drive rotor 260 (FIG. 20) into reciprocation of inner shaft 140 such that inner shaft 140 is both rotated and reciprocated in response to rotation of drive rotor 260 (FIG. 20). Additionally or alternatively, drive assembly 180 may include gearing (not shown) configured to amplify or attenuate the output rotation of inner shaft 140 relative to the input rotation from drive rotor 260 (FIG. 20).

Referring to FIGS. 5 and 6, distal driver 184 of drive assembly 180 is fixed about proximal end portion 142 of inner shaft 140 and includes a proximal body portion 185a, a distal body portion 185b, and lumen 185c extending longitudinally therethrough. Distal driver 184 further includes a collar 186d disposed thereabout between proximal and distal body portions 185a, 185b, respectively. Proximal body portion 185a of distal driver 184 of inner core drive assembly 150 includes a proximal foot 185e extending proximally therefrom. At least a portion of proximal foot 185e defines a non-circular cross-sectional configuration, e.g., a semi-circular, rectangular or other polygonal configuration.

Figure 11:
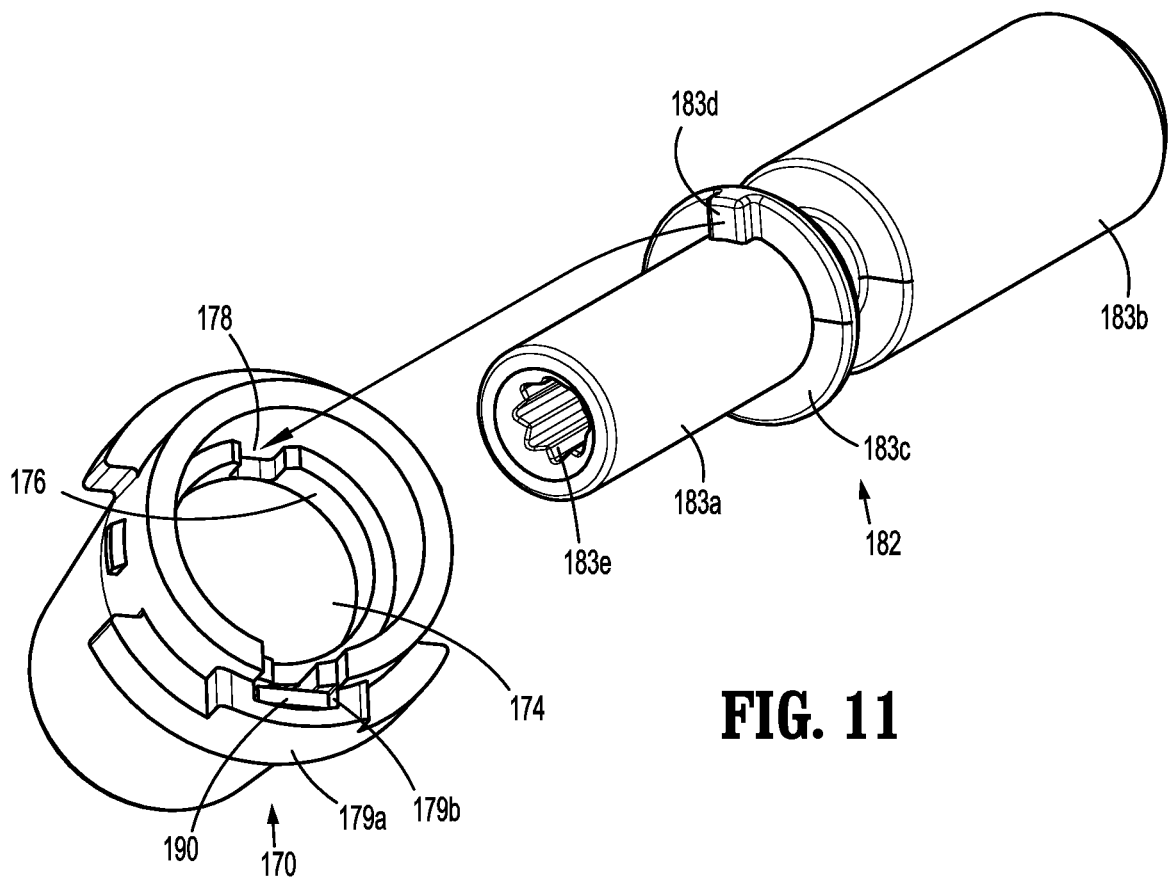
FIG. 11 is an exploded, perspective view illustrating complementary locking features of the retainer cap of FIG. 10 and the proximal driver of FIG. 9.

As illustrated in FIGS. 11, 17, and 18, proximal driver 182 of drive assembly 180 includes a proximal body portion 183a and a distal body portion 183b. Proximal body portion 183a includes an external collar 183c disposed annularly thereabout. External collar 183c includes a proximally-oriented tab 183d that extends therefrom along the exterior surface of proximal body portion 183a. Proximal body portion 183a further includes a proximally-facing cavity 183e at least a portion of which has a non-circular cross-sectional configuration, e.g., an 8-point star or other polygonal configuration, that is configured to at least partially receive drive rotor 260 of handpiece assembly 200 in fixed rotational orientation (see FIG. 20). Distal body portion 183b defines a distally-facing cavity 183f at least a portion of which has a non-circular cross-sectional configuration, e.g., a semicircular, rectangular, or other polygonal configuration. A longitudinally-extending slot 183g defined through a side wall of distal body portion 183b communicates with distally-facing cavity 183f. Distally-facing cavity 183f of proximal driver 182 is configured to slidably receive proximal foot 185e of distal driver 184 in fixed rotational orientation due to the non-circular, and at least partially complementary, configurations thereof. Proximal and distal drivers 182, 184, respectively, cooperate to define a flow path therethrough, e.g., via open proximal end of lumen 183c and longitudinally-extending slot 183g, to enable the suctioning of tissue, fluid, and debris through inner shaft 140, drive assembly 180, through output opening 165 of hub housing 161 and into handpiece assembly 200 (see FIG. 20), as detailed below.

Biasing spring 186 is disposed about proximal body portion 185a of distal driver 184 and includes a distal end that abuts collar 185d of distal driver 184. Biasing spring 186 includes a proximal end that is configured to abut a distal end of distal body portion 183b of proximal driver 182. In this manner, biasing spring 186 biases proximal driver 182 proximally relative to distal driver 184 such that proximally-oriented tab 183d of external collar 183c of proximal body portion 183a of proximal driver 182 is biased into engagement within distally-oriented notch 178 of internal collar 176 of retainer cap 170 to thereby rotationally fix proximal and distal drivers 182, 184 relative to retainer cap 170 and hub housing 161 and, as a result, rotationally fix inner shaft 140 relative to outer shaft 120.

With reference to FIGS. 6-14, the assembly of end effector assembly 100 is detailed. As illustrated in respective FIGS. 6 and 7, pre-assembly of distal driver 184 about proximal end portion 142 of inner shaft 140 in fixed relation relative thereto and pre-assembly of distal body portion 162 of hub housing 161 about proximal end portion 122 of outer shaft 120 in fixed relation relative thereto, is accomplished.

Figure 9:
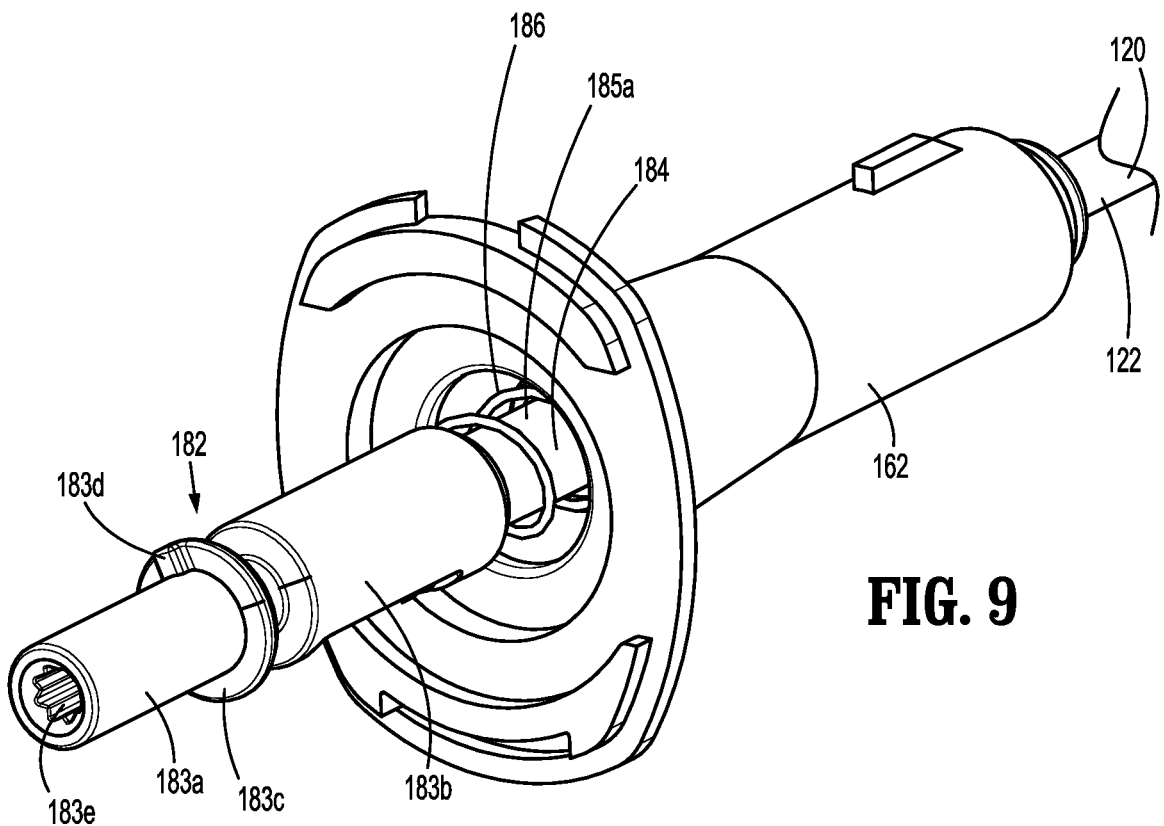
FIG. 9 is a rear, perspective view of the portion of the end effector assembly illustrated in FIG. 8, further including a biasing spring and a proximal driver assembled thereto.

Turning to FIG. 8, once the above-detailed pre-assembly is complete, inner shaft 140 is inserted, in a proximal-to-distal direction, through distal body portion 162 of hub hosing 161 and outer shaft 120. As shown in FIG. 9, biasing spring 186 may then be inserted, in a proximal-to-distal direction, about proximal body portion 185a of distal driver 184 such that the distal end thereof abuts collar 185d of distal driver 184 (see FIGS. 17 and 18). With biasing spring 186 positioned in this manner, proximal driver 182 is slid in a proximal-to-distal-direction onto proximal body portion 185a of distal driver 184 such that distally-facing cavity 183f of proximal driver 182 receives proximal foot 185e of distal driver 184 therein in fixed rotational orientation. This sliding of proximal driver 182 onto distal driver 184 compresses biasing member 186 and, thus, proximal driver 182 is required to be held in position until otherwise retained with hub assembly 160.

Referring to FIG. 12, proximal extension portion 164 of hub housing 161 is slid, in a proximal-to-distal direction, about proximal and distal drivers 182, 184, respectively, and into engagement, e.g., via snap-fitting, with distal body portion 162 of hub housing 161. At this point, proximal driver 182 is still required to be held in position against the bias of biasing member 186, although it is also contemplated that proximal extension portion 164 include features to retain proximal driver 182 in engagement with distal driver 184. Prior to or after the engagement of proximal extension portion 164 with distal body portion 162, O-ring 166 is slid in a proximal-to-distal direction about proximal extension portion 164 of hub housing 161 to be seated within an annular recess 167 defined about proximal extension portion 164 of hub housing 161 distally of outflow opening 165.

Figure 10:
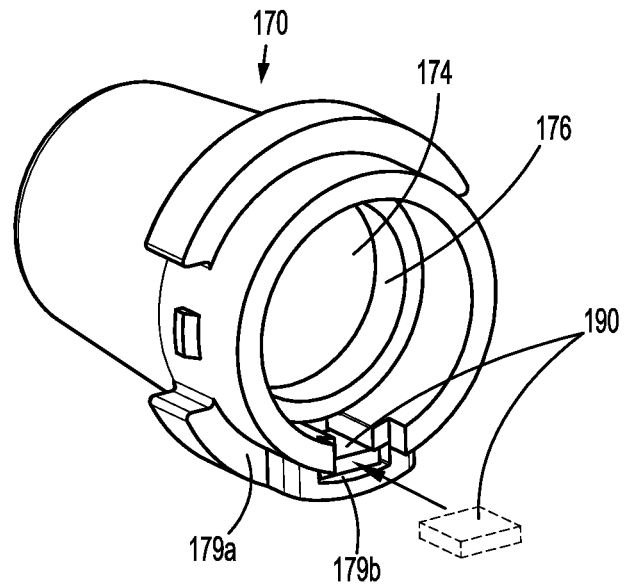
FIG. 10 is a perspective view of a retainer cap of the end effector assembly of FIG. 1 including an RFID chip disposed therein.
Figure 13:
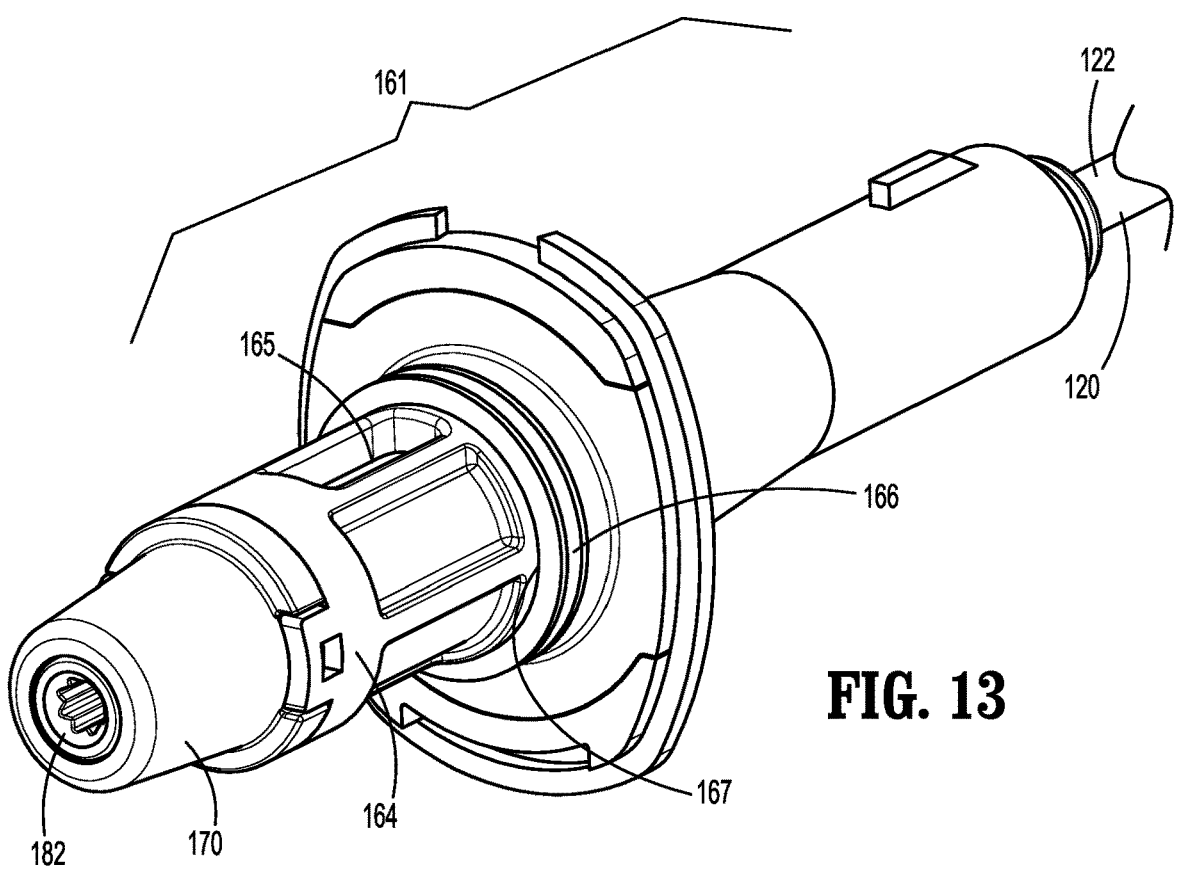
FIG. 13 is a rear, perspective view of the portion of the end effector assembly illustrated in FIG. 12, further including the retainer cap assembled thereto.

With momentary reference to FIG. 10, RFID chip 190 is loaded into pocket 179b of retainer cap 170 and, thereafter, turning to FIG. 13, retainer cap 170 is slid in a proximal-to-distal direction about proximal driver 182 into engagement, e.g., via snap-fitting, with proximal extension portion 164 of hub housing 161. Internal collar 176 of retainer cap 170 defines a diameter less than an outer diameter of external collar 183c of proximal body portion 183a of proximal driver 182 such that proximal driver 182 is inhibited from passing proximally therethrough. As a result, the engagement of retainer cap 170 with proximal extension portion 164 of hub housing 161 retains proximal driver 182 in engagement with distal driver 184 against the bias of biasing spring 186. Accordingly, once retainer cap 170 is engaged with proximal extension portion 164 of hub housing 161, it is no longer required to hold proximal driver 182.

Referring to FIGS. 14-16, outer shell 168 is slid in a distal-to-proximal direction about outer shaft 120 and distal body portion 162 of hub housing 161 into engagement, e.g., via snap-fitting, with distal body portion 162 of hub housing 161 to complete the assembly of end effector assembly 100 (FIG. 1).

Turning to FIGS. 17 and 18, in the fully assembled condition of end effector assembly 100 (FIG. 1), as noted above, biasing spring 186 biases proximal driver 182 proximally such that proximally-oriented tab 183d of external collar 183c of proximal body portion 183a of proximal driver 182 is engaged within distally-oriented notch 178 of internal collar 176 of retainer cap 170 to thereby rotationally fix inner shaft 140 relative to outer shaft 120. End effector assembly 100, e.g., proximal driver 182, distal driver 184, and retainer cap 170 thereof, may be configured such that, in the biased, rotationally locked position, outer shaft window 128 and inner shaft window 148 are disposed in the third position (FIG. 4), corresponding to a closed position of inner shaft 140 relative to outer shaft 120.

Referring to FIGS. 1, 19, and 20, handpiece assembly 200 generally includes handle housing 210, an outflow path 220 defined through handle housing 210 and communicating with an outflow port 400, a motor 250 disposed within handle housing 210, and drive rotor 260 disposed within handle housing 210 and operably coupled to motor 250. Handpiece assembly 200 may further include one or more controls 270, e.g., buttons, disposed on handle housing 210 to facilitate activation of tissue resecting instrument 10, toggle between various modes, and/or to vary the speed of motor 250. Further, outflow tubing (not shown) is configured to connect to outflow port 400 to thereby connect outflow port 400 to a fluid management system (not shown). The fluid management system includes a vacuum source to establish suction through tissue resecting instrument 10 and the outflow tubing to facilitate removal of fluid, tissue, and debris from the surgical site and may also include a collection reservoir, e.g., a collection canister, for collecting the removed fluid, tissue, and debris. As an alternative or in addition to a vacuum source establishing suction through tissue resecting instrument 10 and the outflow tubing, vacuum may be created therethrough via a pressure differential between the surgical site and the outflow path.

Handle housing 210 defines a pencil-grip configuration, although other configurations are also contemplated, e.g., pistol-grip configurations, and includes an open distal end portion 212 communicating with an internal bore 214. Open distal end portion 212 of handle housing 210 provides access to drive rotor 260 and internal bore 214 within handle housing 210 such that, upon engagement of end effector assembly 100 with handpiece assembly 200, as detailed below, a portion of end effector assembly 100 extends through open distal end portion 212 and into internal bore 214 to operably couple with drive rotor 260 and fluidly couple end effector assembly 100 with internal bore 214 and, thus, outflow path 220.

Cable 300 extends proximally from handle housing 210 and is configured to connect to the control unit (not shown) to provide power and control functionality to tissue resecting instrument 10. Cable 300, more specifically, houses one or more wires (not shown) that extend into handle housing 210 and electrically couple controls 270 and motor 250 with the control unit to power motor 250 and control operation of tissue resecting instrument 10 in accordance with controls 270, the control unit, and/or other remote control devices, e.g., a footswitch (not shown). Cable 300 further includes one or more wires 310 that connect to an RFID transceiver 290 disposed within handle housing 210 towards the distal end thereof.

Drive rotor 260 is operably coupled with and extends distally from motor 250 such that, upon activation of motor 250, motor 250 drives rotation of drive rotor 260. Drive rotor 260 defines a base 262 and rotor body 264 extending distally from base 262. Base 262 is stationary and surrounds body 264. Rotor body 264 defines a non-circular cross-sectional configuration, e.g., a square or other polygonal configuration, and is configured for at least partial receipt within proximally-facing cavity 183e of proximal driver 182 of end effector assembly 100 in fixed rotational orientation relative thereto upon engagement of end effector assembly 100 with handpiece assembly 200 such that activation of motor 250 drives rotation of body 264 of drive rotor 260 to, in turn, drive proximal driver 182 of end effector assembly 100.

With reference to FIGS. 1 and 18-20, engagement of end effector assembly 100 with handpiece assembly 200 in preparation for use of tissue resecting instrument 10 is detailed. In order to engage end effector assembly 100 with handpiece assembly 200, end effector assembly 100 is approximated relative to handpiece assembly 200 such that retainer cap 170 and proximal extension 164 of hub housing 161 are inserted into internal bore 214 of handle housing 210 of handpiece assembly 200. As end effector assembly 100 is approximated in this manner, grasping ribs 169c of outer shell 168 of hub assembly 160 of end effector assembly 100 are grasped and squeezed inwardly towards one another, thereby causing the upper and lower surfaces of outer shell 168 to flex outwardly. As the lower surface of outer shell 168 is flexed outwardly, engagement finger 169a and engagement tooth 169b are likewise flexed outwardly. This enables end effector assembly 100 to be approximated further towards handpiece assembly such that engagement tooth 169b is disposed in alignment with and below an engagement aperture 218 defined within handle housing 210 of handpiece assembly 200

Upon release of grasping ribs 169c of outer shell 168, the upper and lower surfaces as well as engagement finger 169a and engagement tooth 169b are returned inwardly towards their initial positions. In this manner, engagement tooth 169b is received within engagement aperture 218 to thereby engage end effector assembly 100 with handpiece assembly 200. Disengagement and release of end effector assembly 100 from handpiece assembly 200 is affected in the opposite manner.

As end effector assembly 100 is approximated relative to handpiece assembly 200 to affect the above-detailed engagement, drive rotor 260 of handpiece assembly 200 is received within proximally-facing cavity 183e of proximal body portion 183a of proximal driver 182 in fixed rotational orientation thereof, e.g., due to the at least partially complementary configurations thereof. Driver rotor 260, more specifically, is inserted within proximally-facing cavity 183e and bottoms out therein prior to engagement of engagement tooth 169b within engagement aperture 218 and, thus, prior to engagement of end effector assembly 100 with handpiece assembly 200. Accordingly, end effector assembly 100 is required to be further approximated relative to handpiece assembly 200 in order to affect engagement. As a result, with rotor body 264 bottomed-out within proximally-facing cavity 183e, further approximation of end effector assembly 100 urges proximal driver 182 distally through and relative to retainer cap 170, against the bias of biasing spring 186, to thereby displace proximally-oriented tab 183d of external collar 183c of proximal body portion 183a of proximal driver 182 from within distally-oriented notch 178 of internal collar 176 of retainer cap 170, thereby rotationally unlocking proximal and distal drivers 182, 184 from retainer cap 170 and hub housing 161. Thus, inner shaft 140 is unlocked from outer shaft 120 and permitted to rotate relative thereto.

With end effector assembly 100 engaged with handpiece assembly 200 as detailed above, RFID chip 190 of end effector assembly 100 is disposed in vertical registration with RFID transceiver 290 of handpiece assembly 200, e.g., wherein RFID transceiver 290 is radially aligned with and disposed radially-outwardly of RFID chip 190 relative to a longitudinal axis defined through end effector assembly 100 and handpiece assembly 200, due to the required orientation of end effector assembly 100 to enable engagement with handpiece assembly 200, e.g., such that engagement tooth 169b is received within engagement aperture 218. Thus, with end effector assembly 100 engaged with handpiece assembly 200, RFID transceiver 290 may read/write data to/from RFID chip 190 and/or communicate read/write data to/from the control unit, e.g., via cable 300.

The data stored on RFID chip 190 of end effector assembly 100 may include item number, e.g., SKU number; date of manufacture; manufacture location, e.g., location code; serial number; use count (which may be updated by writing data from RFID transceiver 290 to RFID chip 190); the home/initial position of inner blade 140; the direction of rotation (clockwise versus counter-clockwise); RPM settings (default, high, medium, low); max RPM; pressure setting information; vacuum setting information; outflow setting information; calibration information; and/or encryption key(s). Additional or alternative data is also contemplated.

Continuing with reference to FIGS. 1 and 18-20, with end effector assembly 100 engaged with handpiece assembly 200 as detailed above, tissue resecting instrument 10 is ready for use. In use, motor 250 of handpiece assembly 200 is activated to drive rotation of drive rotor 260. Upon activation of motor 250, with a head-start or delay relative to activation of motor 250, or independently thereof, suction is established through tissue resecting instrument 10, e.g., via activating the vacuum source of the fluid management system.

Activation of motor 250 drives rotation of drive rotor 260 which, in turn, drives rotation of proximal driver 182 to, in turn, drive rotation of distal driver 184 and thereby rotate inner shaft 140 relative to outer shaft 120. The rotation of inner shaft 140 relative to outer shaft 120, together with the suction applied through inner shaft 140, enables tissue to be drawn through cutting outer shaft window 128 and inner shaft window 148 and inner shaft slot 145, and into inner shaft 140, cut, and suctioned, along with fluids and debris, proximally through inner shaft 140, drive assembly 180, through output opening 165 of proximal extension portion 164 of hub housing 161, and through outflow path 220 of handpiece assembly 200 to outflow port 400 for output to the collection reservoir of the fluid management system.

Upon engagement of end effector assembly 100 with handpiece assembly 200, a control program (not shown) associated with motor 250 may record the rotational position of drive rotor 260 as a home position and, after activation, ensure that drive rotor 260 stops at a rotational position corresponding to the home position, e.g., the closed position of inner shaft 140 relative to outer shaft 120 such that inner shaft window 128 is not aligned with outer shaft window 148 (FIG. 4). The control program may utilize correlation information, e.g., from RFID chip 190, correlating, for example, rotation of drive rotor 260 with rotation of inner shaft 140 to ensure that inner shaft 140 is returned to the closed position relative to outer shaft 120 after each activation. Returning to the home position, corresponding to the closed position of inner shaft 140, also returns proximal driver 182 to its initial rotational position whereby proximally-oriented tab 183d of external collar 183c of proximal body portion 183a of proximal driver 182 is rotationally aligned with distally-oriented notch 178 of internal collar 176 of retainer cap 170. As such, upon disengagement and withdrawal of end effector assembly 100 from handpiece assembly 200, biasing spring 186 returns proximal driver 182 proximally to thereby bias proximally-oriented tab 183d into engagement within distally-oriented notch 178 to re-engage the rotational lock rotationally fixing inner shaft 140 in the closed position relative to outer shaft 120.

Referring generally to FIG. 19, as an alternative to handpiece assembly 200 configured for manual grasping and manipulation during use, tissue resecting instrument 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely controls the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue-resecting device, the end effector assembly comprising:
an outer shaft including a proximal end portion, a distal end portion, and an outer shaft window defined within the distal end portion, the outer shaft window defining an outer shaft cutting edge extending about at least a portion of a perimeter thereof, the outer shaft cutting edge including a plurality of teeth;
an inner shaft disposed within and rotatable relative to the outer shaft, the inner shaft including a proximal end portion, a distal end portion, and an inner shaft window defined within the distal end portion, the inner shaft window defining an inner shaft cutting edge extending about at least a portion of a perimeter thereof, the inner shaft cutting edge being toothless, wherein rotation of the inner shaft relative to the outer shaft causes the inner shaft cutting edge to rotate toward the outer shaft cutting edge, wherein the inner shaft includes a distal driver disposed about the proximal end portion thereof;
a proximal driver slidably coupled to the distal driver in a fixed rotational orientation relative thereto such that rotation of the proximal driver drives rotation of the distal driver;
a retainer cap defining a pocket having an open end, the retainer cap disposed about at least a portion of the proximal driver and fixedly engaged with a hub housing of the outer shaft to thereby fix the retainer cap relative to the hub housing and the outer shaft, the retainer cap configured to selectively lock the proximal driver in fixed rotational orientation relative thereto, thereby selectively locking the inner shaft relative to the outer shaft; and a radiofrequency identification chip (RFID chip) disposed within the pocket, wherein, with the retainer cap engaged with the hub housing, a portion of the hub housing closes the open end of the pocket to retain the RFID chip therein.

2. The end effector assembly according to claim 1, wherein a distal end of the outer shaft window is disposed proximally of a distal-most end of the outer shaft.

3. The end effector assembly according to claim 2, wherein the distal-most end of the outer shaft is blunt.

4. The end effector assembly according to claim 1, wherein the distal end portion of the inner shaft includes only one inner shaft cutting edge.

5. The end effector assembly according to claim 1, wherein the distal end portion of the outer shaft includes an outer shaft slot disposed opposite the outer shaft window.

6. The end effector assembly according to claim 1, wherein the distal end portion of the inner shaft includes an inner shaft slot disposed opposite the inner shaft window at a proximal end of the distal end portion of the inner shaft.

7. The end effector assembly according to claim 1, wherein the inner shaft cutting edge defines a length, and wherein an entirety of the length of the inner shaft cutting edge is defined by a single curve.

8. The end effector assembly according to claim 1, further comprising a biasing spring extending between the proximal driver and the distal driver, the biasing spring configured to bias the proximal driver towards a locked position, wherein the retainer cap locks the proximal driver in fixed rotational orientation relative thereto.

9. The end effector assembly according to claim 8, wherein the proximal driver is movable against the bias of the biasing spring to an unlocked position, wherein the proximal driver is unlocked from the retainer cap to permit relative rotation therebetween.

10. A tissue resecting instrument, comprising:
a handpiece assembly;
an end effector assembly extending distally from the handpiece assembly and defining a longitudinal axis, the end effector assembly including:
an elongated outer shaft having a distal end portion with an outer shaft window defined therein, the outer shaft window including a plurality of teeth surrounding at least a portion of a perimeter thereof;
an elongated inner shaft disposed coaxially with the elongated outer shaft, the elongated inner shaft having a distal end portion with an inner shaft window defined therein, the inner shaft window at least partially bounded by a toothless, inner shaft cutting edge, the elongated inner shaft rotatable about the longitudinal axis relative to the elongated outer shaft such that the inner shaft cutting edge rotates toward the plurality of teeth of the outer shaft window;
a distal driver disposed about a proximal end portion of the elongated inner shaft and a proximal driver slidably coupled to the distal driver, the proximal driver configured to drive rotation of the distal driver;
a retainer cap disposed about at least a portion of the proximal driver and engaged to the elongated outer shaft, the retainer cap configured to selectively lock the proximal driver in fixed rotational orientation relative thereto thereby selectively locking the elongated inner shaft relative to the elongated outer shaft; and
a radiofrequency identification chip (RFID chip) engaged with the retainer cap, wherein, with the retainer cap engaged to the elongated outer shaft, a portion of the elongated outer shaft retains the RFID chip in engagement with the retainer cap.

11. The tissue resecting instrument according to claim 10, wherein the handpiece assembly includes an outflow port configured to connect to a fluid management system.

12. The tissue resecting instrument according to claim 10, wherein the handpiece assembly includes a motor configured to cause rotation of the elongated inner shaft relative to the elongated outer shaft.

13. The tissue resecting instrument according to claim 10, wherein a distal end of the outer shaft window is disposed proximally of a distal-most end of the elongated outer shaft.

14. The tissue resecting instrument according to claim 10, wherein the distal end portion of the elongated inner shaft includes only one inner shaft cutting edge.

15. The tissue resecting instrument according to claim 10, wherein the distal end portion of the elongated outer shaft includes an outer shaft slot disposed opposite the outer shaft window.

16. The tissue resecting instrument according to claim 10, wherein the inner shaft cutting edge defines a length, and wherein an entirety of the length of the inner shaft cutting edge is defined by a single curve.

17. A tissue resecting instrument, comprising:
a handpiece assembly;
an end effector assembly extending distally from the handpiece assembly and defining a longitudinal axis, the end effector assembly including:
an outer shaft having a distal end portion with an outer shaft window defined therein, the outer shaft window including a plurality of teeth surrounding at least a portion of a perimeter thereof;
an inner shaft disposed coaxially with the outer shaft, the inner shaft having a distal end portion with an inner shaft window defined therein, the inner shaft window at least partially bounded by an inner shaft cutting edge, the inner shaft rotatable about the longitudinal axis relative to the outer shaft such that the inner shaft cutting edge rotates toward the plurality of teeth of the outer shaft window;
a distal driver disposed about a proximal end portion of the inner shaft and a proximal driver coupled to the distal driver, the proximal driver configured to drive rotation of the distal driver;
a retainer cap disposed about at least a portion of the proximal driver and engaged to the outer shaft, the retainer cap configured to selectively lock the proximal driver in fixed rotational orientation relative thereto thereby selectively locking the inner shaft relative to the outer shaft; and
a radiofrequency identification chip (RFID chip) secured in engagement with the retainer cap by a portion of the outer shaft.

18. The tissue resecting instrument according to claim 17, further comprising a hub housing operably engaged to the outer shaft and configured to retain the RFID chip within a pocket defined in the retainer cap.

19. The tissue resecting instrument according to claim 17, wherein a distal end of the outer shaft window is disposed proximally of the distal end portion of the outer shaft.

20. The tissue resecting instrument according to claim 17, wherein the distal end portion of the outer shaft includes an outer shaft slot disposed opposite the outer shaft window.

* * * * *